(12) United States Patent
McClellan

(10) Patent No.: US 10,420,920 B2
(45) Date of Patent: Sep. 24, 2019

(54) LOTION APPLICATION MACHINE WITH ROTATABLE PLATFORM

(71) Applicant: SNAPPYSCREEN, INC., Locust Valley, NY (US)

(72) Inventor: Kristen McClellan, Locust Valley, NY (US)

(*) Notice: Subject to any disclaimer, the term of this patent is extended or adjusted under 35 U.S.C. 154(b) by 0 days.

(21) Appl. No.: 15/620,566

(22) Filed: Jun. 12, 2017

(65) Prior Publication Data

US 2017/0361349 A1    Dec. 21, 2017

Related U.S. Application Data

(63) Continuation-in-part of application No. 14/685,969, filed on Apr. 14, 2015, now abandoned.

(60) Provisional application No. 61/979,417, filed on Apr. 14, 2014.

(51) Int. Cl.
| | |
|---|---|
| *A61M 35/00* | (2006.01) |
| *A45D 34/00* | (2006.01) |
| *B05B 13/02* | (2006.01) |
| *B05B 16/40* | (2018.01) |
| *B05B 15/65* | (2018.01) |
| *B05C 13/02* | (2006.01) |

(52) U.S. Cl.
CPC ............. *A61M 35/25* (2019.05); *A45D 34/00* (2013.01); *B05B 13/0242* (2013.01); *B05B 13/0285* (2013.01); *B05B 15/65* (2018.02); *B05B 16/405* (2018.02); *A45D 2034/005* (2013.01); *A61M 35/00* (2013.01); *B05B 13/0228* (2013.01); *B05C 13/02* (2013.01)

(58) Field of Classification Search
CPC ... B05B 16/40; B05B 13/0242; B05B 16/405; B65G 29/00; B23P 21/006; A61M 35/00; A61M 35/20; A61M 35/25
See application file for complete search history.

(56) References Cited

U.S. PATENT DOCUMENTS

| 5,784,932 A * | 7/1998 | Gilberti | B23Q 15/26 |
| | | | 108/22 |
| 5,950,503 A * | 9/1999 | Amendolea | B23P 21/006 |
| | | | 74/813 C |
| 6,402,774 B1 * | 6/2002 | Caldironi | A61N 5/0614 |
| | | | 128/898 |
| 8,597,263 B2 * | 12/2013 | Hipperson | A01K 13/001 |
| | | | 454/49 |
| 2006/0275555 A1* | 12/2006 | Colizza | B05B 16/40 |
| | | | 427/458 |
| 2006/0278661 A1* | 12/2006 | Cooper | B05B 5/03 |
| | | | 222/321.1 |
| 2010/0065655 A1* | 3/2010 | Hipperson | A01K 13/001 |
| | | | 239/99 |

* cited by examiner

*Primary Examiner* — Karl Kurple
(74) *Attorney, Agent, or Firm* — Scully Scott Murphy and Presser

(57) ABSTRACT

A lotion application machine for allowing automatic application of a lotion to the body of a user is provided. The lotion application machine has a rotatable platform, on which the user can stand and be rotated while the lotion is being applied. The lotion can be applied evenly to the entire body of the user.

7 Claims, 30 Drawing Sheets

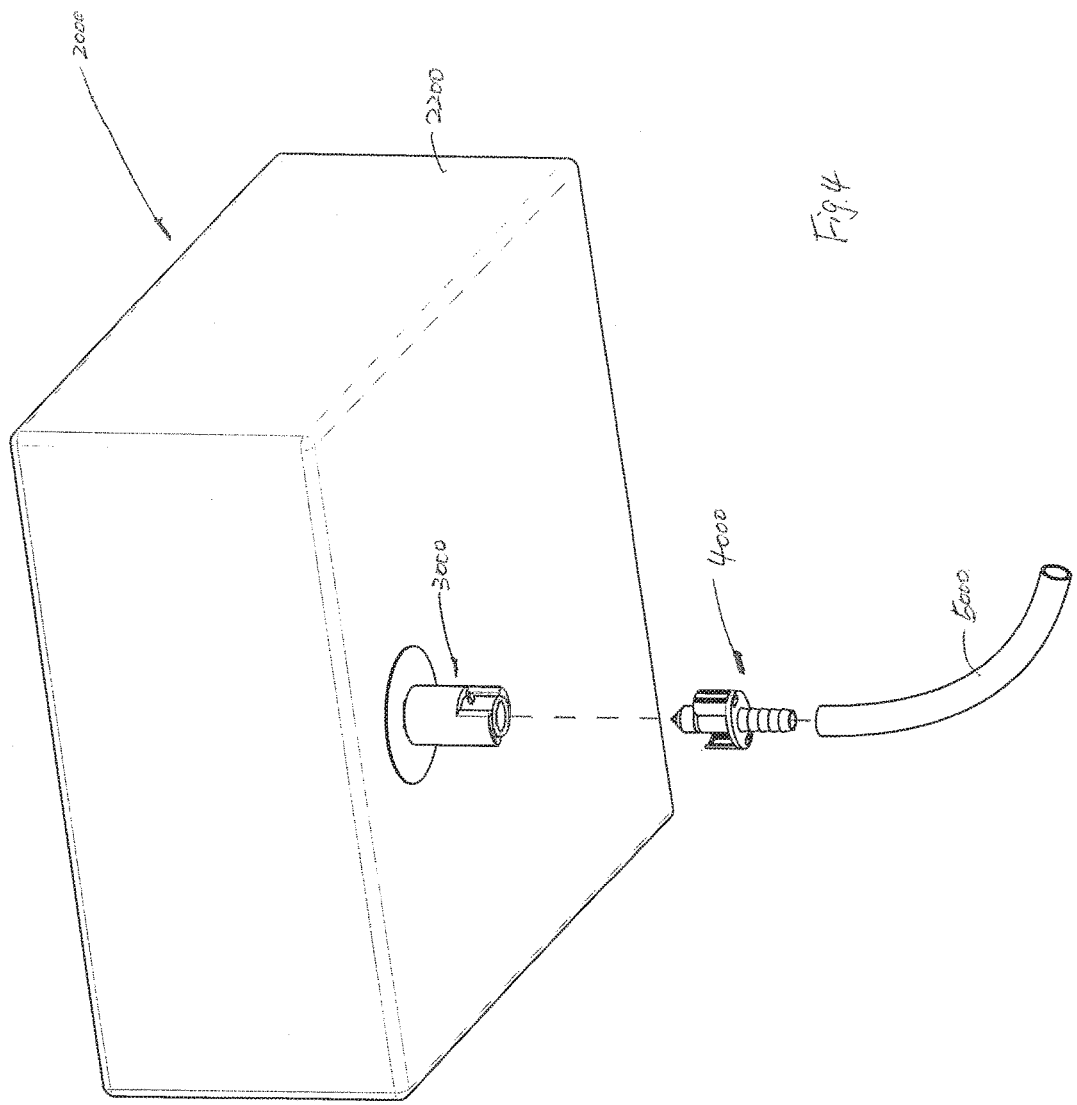

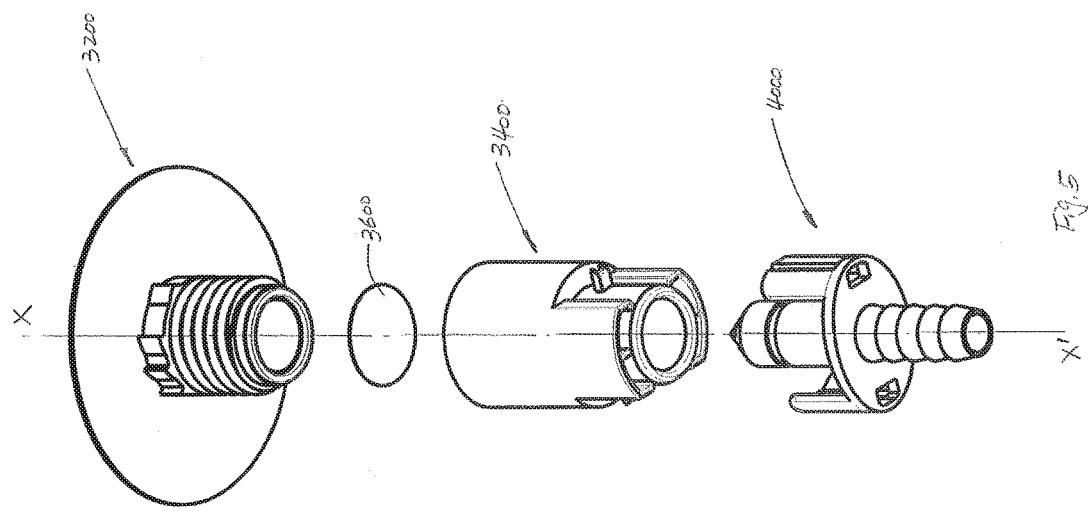
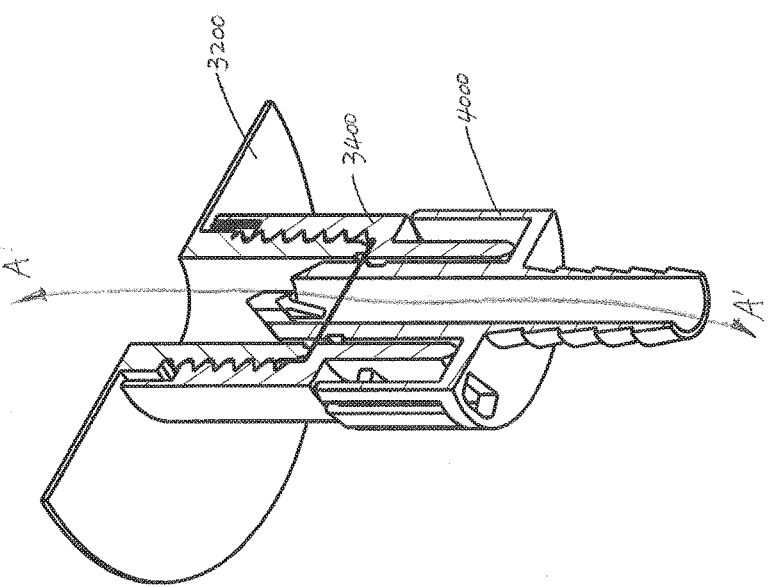

LOTION APPLICATION MACHINE WITH ROTATABLE PLATFORM

CROSS REFERENCE TO RELATED APPLICATIONS

The present application is a continuation-in-part application of U.S. application Ser. No. 14/685,969 filed on Apr. 14, 2015, which claims benefit of U.S. Provisional Application No. 61/979,417 filed on Apr. 14, 2014, all of the contents of which are incorporated herein by reference for all purposes.

FIELD

The present disclosure relates generally to the field of applying lotion to a human body, and more particularly to a machine for selectively applying lotion and replaceable cartridges used in connection with the machine for accommodating a selection of lotion.

BACKGROUND

When people are at a beach, pool, resort or other outdoor areas, they intend to apply lotion, such as sunscreen, to protect their skin, normally by squeezing the lotion from a bottle into their hands. Subsequently, the lotion is applied by manually rubbing it to the skin. This application process does not allow the user to reach all their skin, and also results in uneven distribution of the lotion. Thus, improved method and devices for applying lotions is desirable.

BRIEF SUMMARY

As described herein, the exemplary embodiments of the current invention overcome one or more of the above and other disadvantages known in the art.

An exemplary aspect of the present invention relates to a lotion application machine. The machine includes: a platform for placing the lotion application machine on an under-support, wherein the platform has a top surface for supporting a user of the lotion application machine; a continuous circumference on the platform for defining a lotion application space; at least one lotion applying section provided to the continuous circumference and comprising at least one spray nozzle for spraying a lotion into the lotion application space; a refillable cartridge for storing the lotion; a tubing for delivering the lotion from the refillable cartridge to the at least one lotion applying section, wherein the tubing comprising a fitting member for detachably connecting the refillable cartridge to the tubing; and an operation station comprising a user interface for allowing the user to activate the at least one lotion applying section to spray the lotion into the lotion application space.

These and other aspects and advantages of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and, unless otherwise indicated, the drawings are merely intended to conceptually illustrate the structures and procedures described herein.

BRIEF DESCRIPTION OF THE SEVERAL VIEWS OF THE DRAWINGS

FIG. 4 is a perspective view of a cartridge having a connector according to another aspect of the present application;

FIG. 5 is an exploded perspective view of the connector to be connected to a fitting member of the lotion application machine;

FIG. 6 is a sectional view of the assembled connector and fitting member along the middle of the assembly;

DETAILED DESCRIPTION

Figure 1:
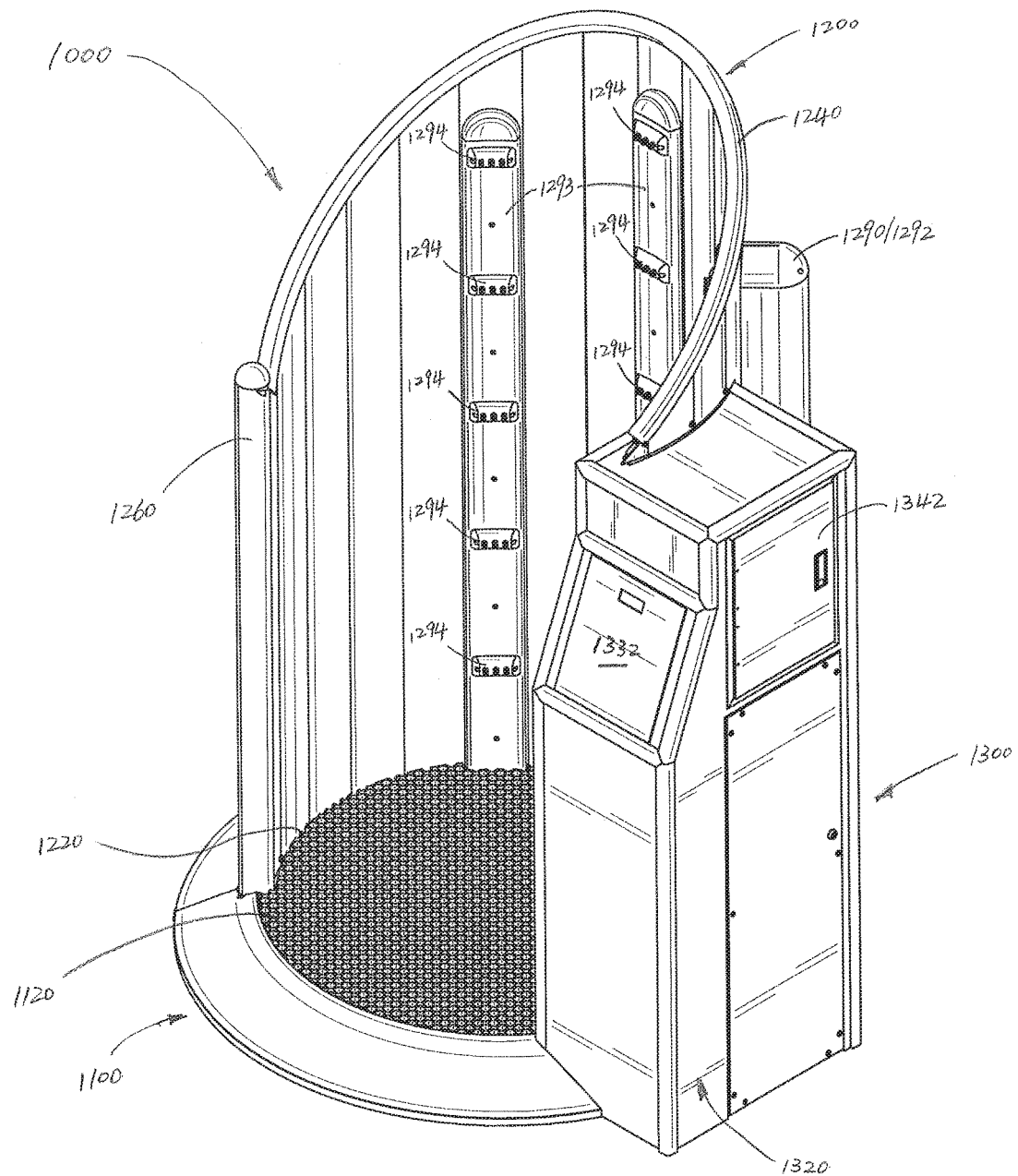
FIG. 1 is a perspective view of a lotion application machine according to an aspect of the present application.
Figure 2:
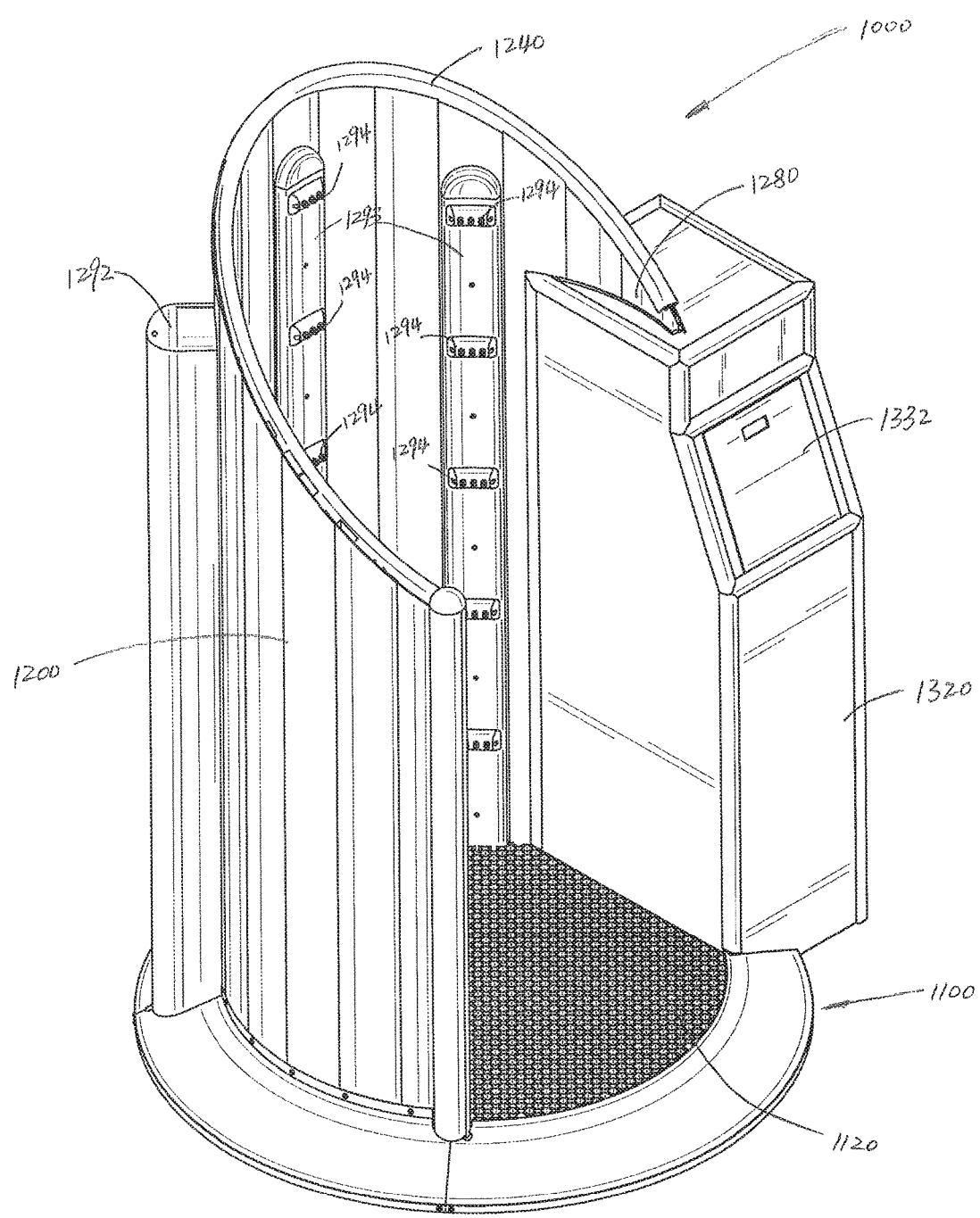
FIG. 2 is another perspective view of the lotion application machine.
Figure 3:
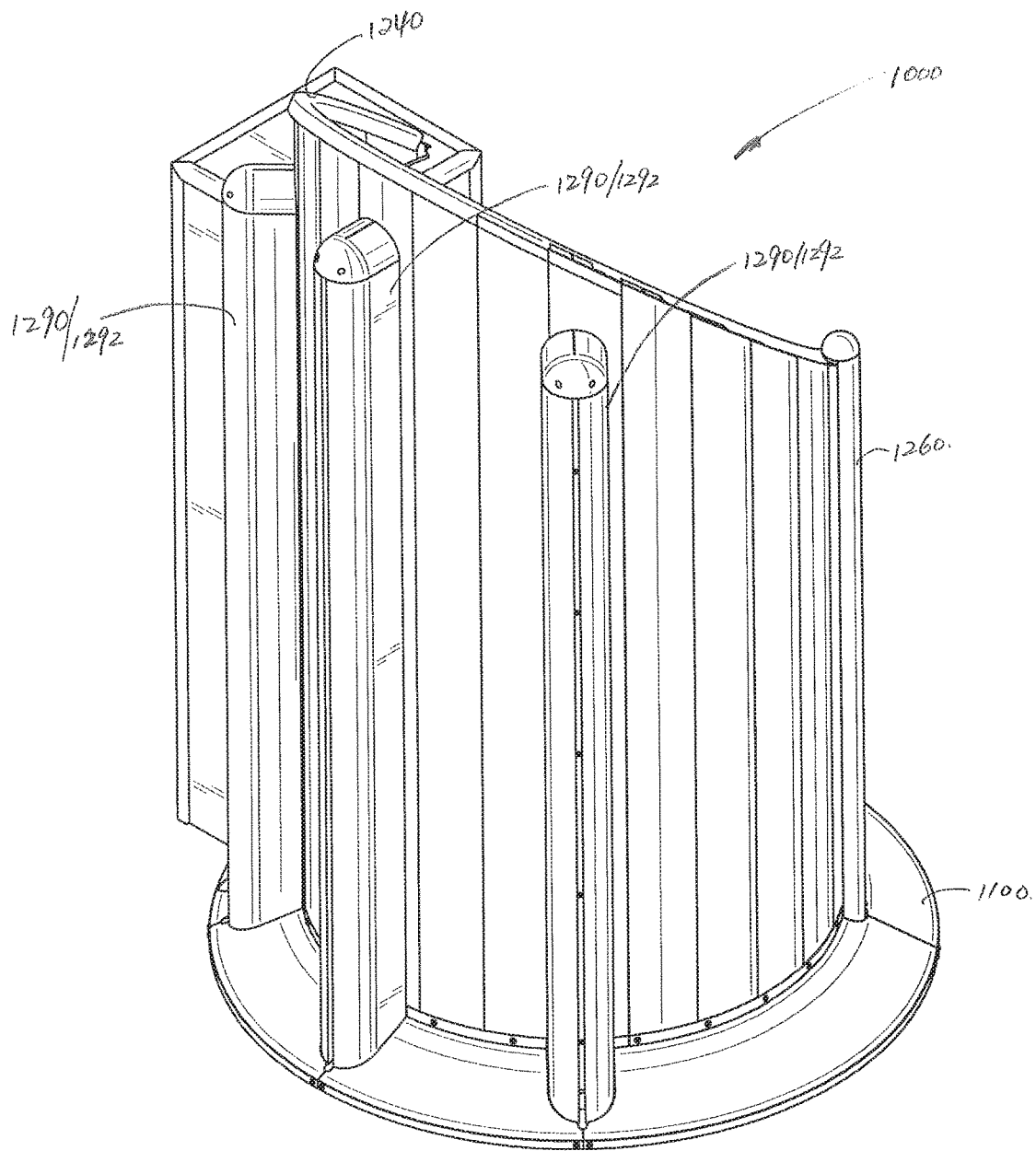
FIG. 3 is yet another perspective view of the lotion application machine.
Figure 7:
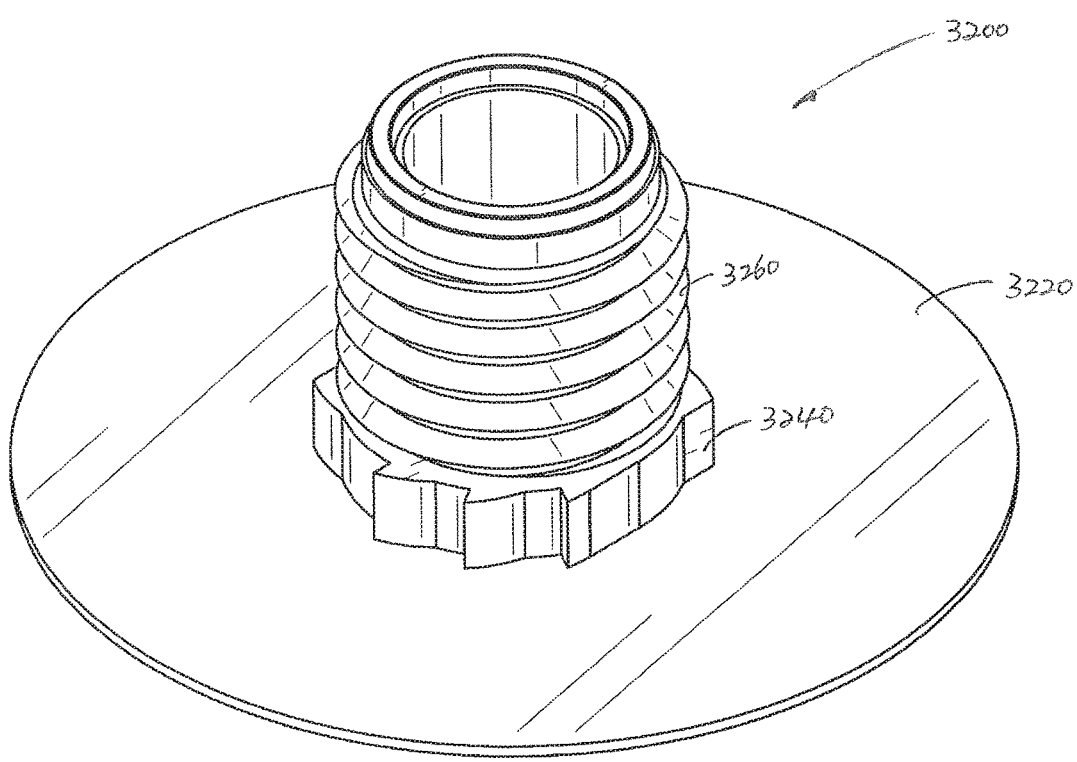
FIG. 7 is a perspective view of a base of the connector shown in FIG. 5.
Figure 8:
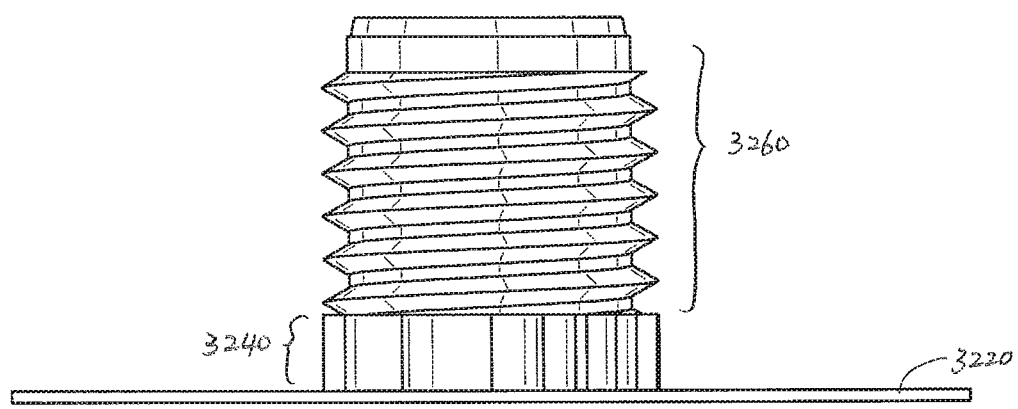
FIG. 8 is a side view of the base shown in FIG. 7.
Figure 9:
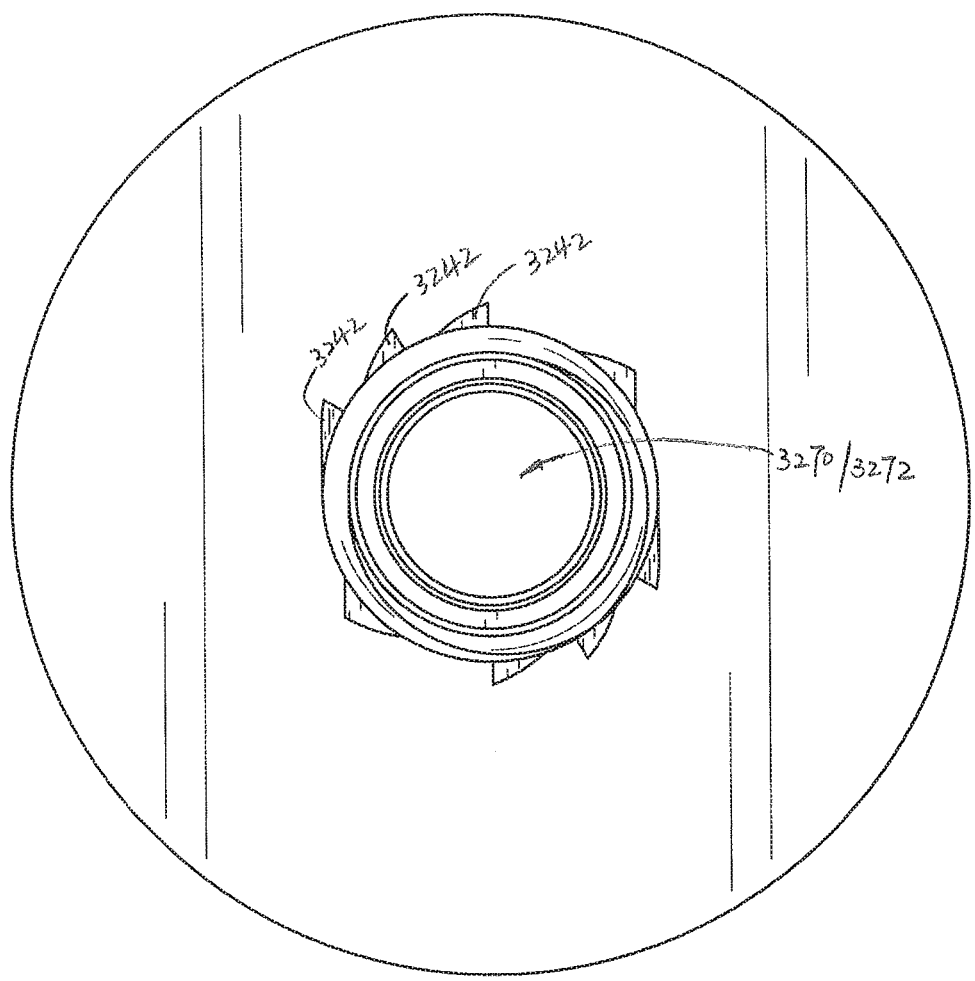
FIG. 9 is a top view of the base shown in FIG. 7.
Figure 10:
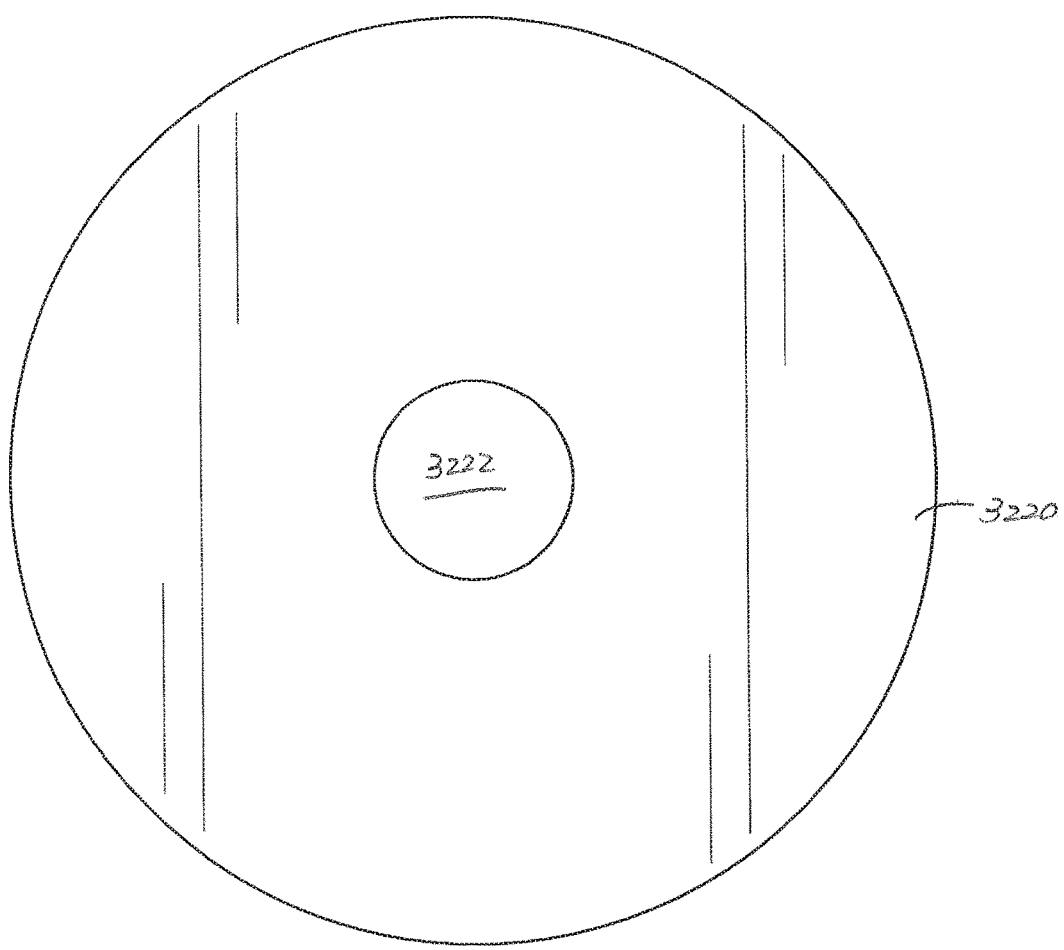
FIG. 10 is a bottom view of the base shown in FIG. 7.

FIGS. 1-3 illustrate a lotion application machine 1000 which can be used to automatically apply lotion, such as sunscreen, to a human body. The machine 1000 includes a platform 1100, through which the machine 1000 is secured to the ground or a floor. Optionally, the platform 1100 has an anti-slippery layer 1120, which is constructed of anti-slippery features (such as, bumps) and/or made of a material having anti-slippery characteristics (such as, silicone). The platform 1100 can be of any suitable shape, such as circular, depending on the design consideration of the machine. Optionally, the platform 1100 can have retractable wheels and anchors, which render the machine mobile.

The machine 1000 further includes a wall 1200. The wall 1200 is continuous to define generally the circumference of the lotion application machine 1000, which circumference provides a space for applying lotion to a human body. The wall 1200 is connected to the platform 1100 through a bottom edge 1220, which edge can substantially correspond to the profile of the anti-slippery layer 1120. The wall 1200 also has a top edge 1240, which is vertically opposite the bottom edge 1220 and can be angled with respect to the bottom edge 1220. The top edge 1240 can be curved or ornamented to enhance the appearance and aesthetics of the machine. For example, in the shown embodiment, the wall 1200 forms a partial cylinder with an entrance opening to accommodate a person stepping onto the platform 1100, but other profiles are applicable.

The wall 1200 has a first lateral end 1260 and a second lateral end 1280 that is merged with an operation station 1300 of the lotion application machine 1000, as best shown in FIG. 2. The first lateral end 1260 and the operation station 1300 together define an opening, through which a user can enter or exit the space defined by the wall 1200 for applying lotion. Optionally, a door can be provided to allow access to the space. In one example, access to the space may be subject to the user's payment to use the machine.

The wall 1200 further includes a plurality of lotion applying sections 1290, as shown in FIGS. 1-3. Each applying section 1290 includes an outer column 1292 disposed at the external side of the wall 1200, and an inner column 1293 disposed at the inner side of the wall 1200. The inner column 1293 includes a plurality of spray nozzles 1294. The outer column 1292 provides a space, within which various tubings, fittings, valves and/or pumps can be provided to transport lotions from a storage (which will be described later) in the operation station 1300 to the spray nozzles 1294. Optionally, the platform 1100 may also include various tubings, fittings, valves and/or pumps to facilitate distributing and transporting lotions from the storage to the spray nozzles 1294. Through all these tubings, fittings, valves and/or pumps, the spray nozzles 1294 are in fluid communication with the storage and thus, can be controlled to spray the lotions according to instructions from the operation station 1300. In each lotion applying section 1290, the spray nozzles 1294 are provided at various heights to accommodate the needs of different people. In addition, the plurality of applying sections 1290 are circumferentially distributed along the inner side of the wall 1200, to allow application of lotion from various angles, thereby achieving a satisfactory applying result.

The operation station 1300 includes a control section 1320, which allows interaction between the user and the machine to properly manage the payment and also controls the distribution and transportation of the lotions based on the input of the user.

The control section 1320 includes an interface 1322, such as a touch screen, through which the user initiates the operation of the machine 1000 by touching the available options shown on the interface. The interface 1322 can show a virtual keyboard for the user to input the user's payment information, or include a hardware reader (such as a scanner or a card reader) for reading the payment information. The control section 1320 further includes a processor, which functions to process data received from the user and control the application of lotion based on the result of the data processing, such as, the types of the lotion to be applied, the lasting time for applying the lotion, the density of the lotion to be applied, the location of the lotion to be applied and so on. The control section 1320 further includes a power supply, which can be a battery pack or a connection to an external power line. The power supply provides electricity to the control section 1320 and the pumps and valves of the machine, for transporting lotion to the spray nozzles 1294. The control section 1320 can have other suitable units or blocks for performing other functions, such as an alarm unit for sending alarms when the machine is being tampered, a calculation section for generating an optimum pattern for applying lotion based on the different human anatomies and for tracking usage information that can be used for repurchase of lotion by the machine owner, among other functions.

The operation station 1300 further includes a lotion storage, which can include one or more replaceable cartridges 2000 as shown in FIG. 4. Each cartridge 2000 contains a predetermined amount and type of lotion. The cartridge 2000 is placed through a door 1342 and is replaceable upon depletion of the lotion in the cartridge.

FIG. 4 is a perspective view of the cartridge 2000, being isolated from the machine for better clarity. The cartridge 2000 includes a container 2200 within which the predetermined amount and type of lotion is stored. The container 2200 can be a box made of suitable materials, as shown in this embodiment. The container 2200 can directly receive and store lotion; alternatively, the lotion can be stored in a plastic bag which is in turn placed in the container 2200.

The cartridge 2000 also includes a connector 3000 protruding from an outer surface of the container 2200, for operatively connecting the cartridge 2000 to a downstream fitting member 4000 which is in turn connected to a tube 5000.

The connector 3000 allows the lotion within the container 2200 to be delivered to the spray nozzles 1294 upon assembling the fitting member 4000 with the connector 3000. The fitting member 4000 and the tube 5000 together form a part of the lotion delivery system of the machine 1000.

The fitting member 4000 and the tube 5000 are pre-connected to other tubes, fitting and/or valves to establish a fluid communication with the spray nozzles 1294. In use, an operator of the machine manually place the cartridge 2000 in the machine 1000 above the fitting member 4000 and snap-fits the fitting member 4000 onto the connector 3000 or vice versa.

FIG. 5 is an exploded perspective view of the connector 3000 and the fitting member 4000; FIG. 6 is a sectional view of the connector 3000 and the fitting member 4000 after they are assembled.

The connector 3000 includes a base 3200 and a locking section 3400, which can be operatively attached to each other, through for example threaded connection.

The base 3200 is shown in FIGS. 7-10. The base 3200 will be described with respect to its relative bottom and top orientations (or lower and upper orientations) as shown in the figures; however, a skilled person in the art understands that these orientations can be reversed in practice.

The base 3200 includes a bottom plate 3220, which can be a circular planar plate, as in the shown embodiment, although other profiles are contemplatable and within the scope of the present application. The bottom plate 3220 is integrally formed with the container 2200 or a component of the container 2200 (such as, a plastic bag within the container) during manufacture, and cannot be separated from the container 2200 without damaging the integrity of the bottom plate and the container. For example, the bottom plate 3220 can be thermally sealed to the container 2200 or the plastic bag of the container 2200 during manufacture.

The bottom plate 3220 defines a bottom opening 3222, through which the lotion of the container 2200 can be transported to the tube 5000.

The base 3200 further includes a toothed portion 3240 provided on the bottom plate 3220 and a threaded portion 3260 provided on the toothed portion 3240. The toothed portion 3240 and the threaded portion 3260 collectively provide a connection portion of the base 3200 for connecting the locking section 3400.

In operation, the threaded portion 3260 operatively mates a corresponding threaded portion of the locking section 3400 to connect the base 3200 to the locking section 3400, and subsequently, the toothed portion 3240 operatively mates a corresponding toothed portion of the locking section 3400 to prevent disengagement between the base 3200 and the locking section 3400. Both the toothed portion 3240 and the threaded portion 3260 are tubular, to collectively define a through hole 3270 that is continuous with the bottom opening 3222 of the bottom plate. The threaded portion 3260 is substantially cylindrical. The toothed portion 3240 includes a plurality of teeth 3242 distributed evenly or unevenly along the circumference of the toothed portion 3240. When viewed from the top of the base 3200, each tooth 3242 has a substantially triangular shape.

The through hole 3270 has a top opening 3272, which is sealed by a sealing member, such as a membrane 3600 (shown in FIG. 5). The membrane 3600 is sealed to the top opening 3272 to temporarily insulate the lotion in the container 2200 from the outside environment, yet is breakable by a pointed tip of the fitting member 4000 once the fitting member 4000 is assembled to the connector 3000 to allow the lotion to be delivered from the container 2200 to the tube 5000.

The locking section 3400 is shown in FIGS. 11-15. The locking section 3400 will be described with respect to its relative bottom and top orientations (or lower and upper orientations) as shown in the figures; however, a skilled person in the art understands that these orientations can be reversed in practice.

The locking section 3400 engages and substantially encloses the threaded portion 3260 and toothed portion 3240 of the base 3200. Once the locking section 3400 fully engages the base 3200, the locking section 3400 exerts pressure onto the membrane 3600, particularly along the periphery of the membrane 3600, such that when the membrane 3600 is being pierced by the tip of the fitting member 4000, the membrane 3600 is surface tensioned. In addition, the action of firmly sandwiching the membrane 3600 between the locking section 3400 and the base 3200, will prevent the membrane 3600 from being accidentally or inadvertently removed and also deter tampering or unauthorized handling of the lotion by removing and reattaching the membrane, during transportation or other handling of the cartridge 2000.

In addition, once the cartridge 2000 is assembled into the application machine 1000, the locking section 3400 engages the fitting member 4000 to lock the connector 3000 with the fitting member 4000. During this locking process, a pointed tip of the fitting member 4000 pierces the membrane 3600, thereby establishing a fluid communication between the cartridge 2000 and the tube 5000, as shown by the arrows A-A' in FIG. 6.

For this purpose, the locking section 3400 includes a lower portion 3420 for engaging the base 3200 and an upper portion 3440 for engaging the fitting member 4000. Both the lower portion 3420 and the upper portion 3440 are tubular to collectively define a through hole 3460 extending throughout the vertical dimension of the locking section 3400. The through hole 3460 has a top opening 3462. For example, the locking section 3400 can be substantially cylindrical, extending symmetrically along an axis X-X'.

Figure 14:
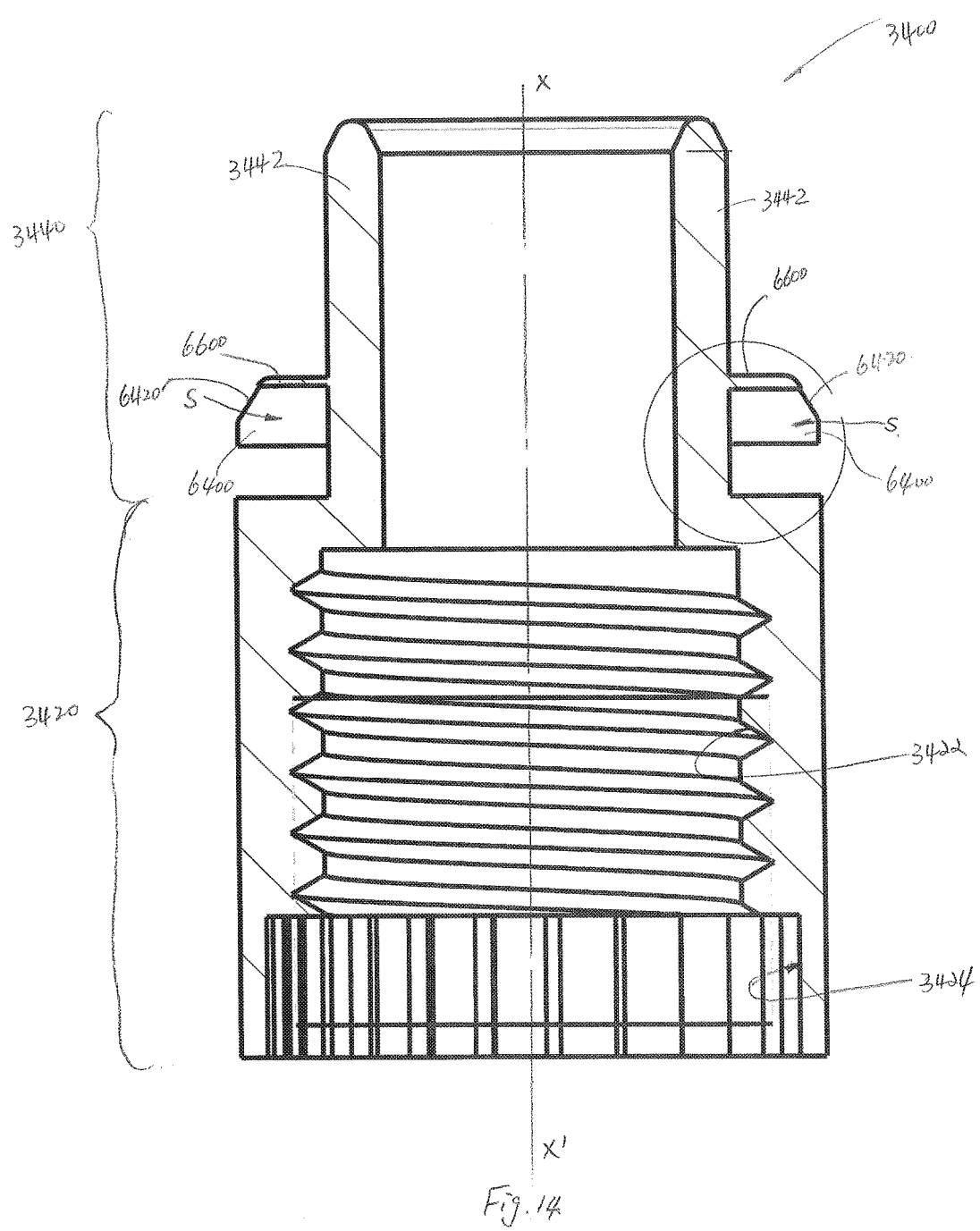
FIG. 14 is a sectional view along lines 14-14 of FIG. 13.
Figure 15:
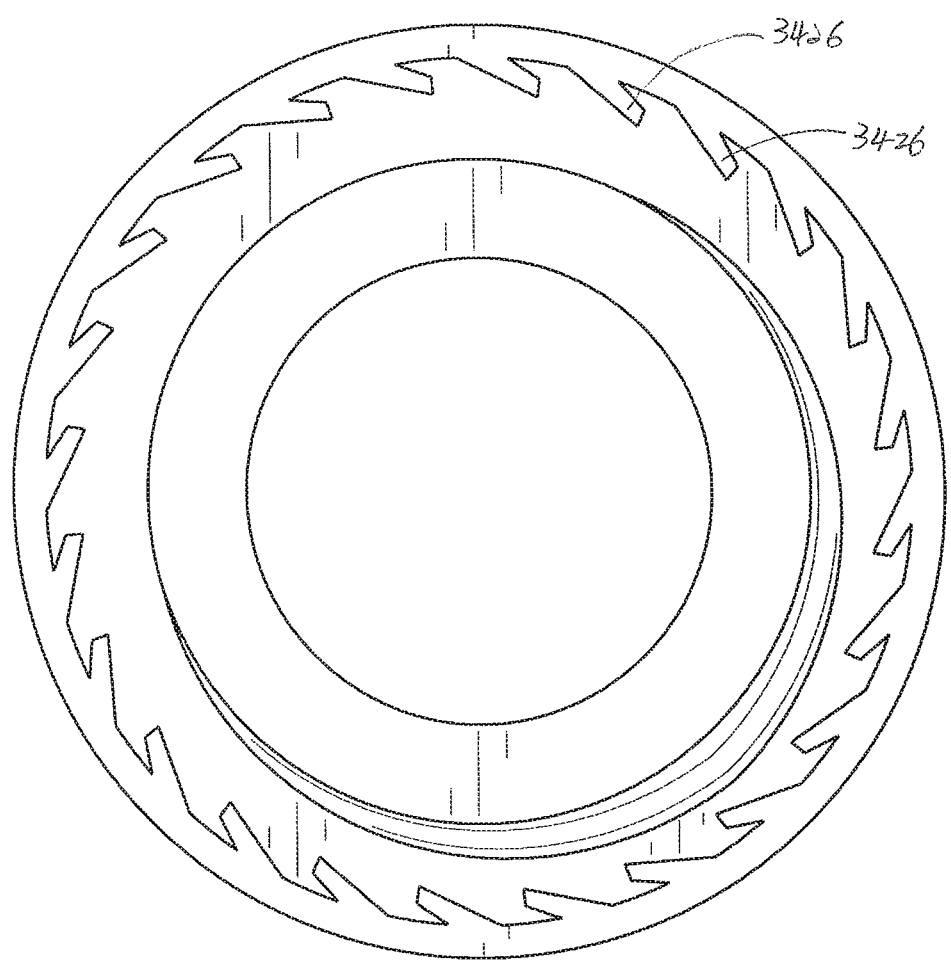
FIG. 15 is a bottom view of the locking section shown in FIG. 11.

As shown in FIG. 14, the tubular lower portion 3420 includes an inner threaded portion 3422 and an inner toothed portion 3424. The inner threaded portion 3422 has internal threads, through which the inner threaded portion 3422 operatively engages the external threads of the threaded portion 3260 of the base 3200. The vertical dimensions of the inner threaded portion 3422 and threaded portion 3260 are properly adapted, such that when these threaded portions completely engage each other, the inner toothed portion 3424 of the locking section 3400 and the toothed portion 3240 of the base 3200 partially or completely engage each other. The inner toothed portion 3424 of the locking section 3400 and the toothed portion 3240 of the base 3200 are adapted, such that, once they at least partially engage each other, a reverse operation to detach the locking section 3400 from the base 3200 is prohibited. This configuration enhances the tamper-proof characteristics of the cartridge 2000. For this purpose, the inner toothed portion 3424 of the locking section 3400 includes a plurality of teeth 3426 distributed along the internal circumference of the lower portion 3420, as shown in FIG. 15.

Figure 16:
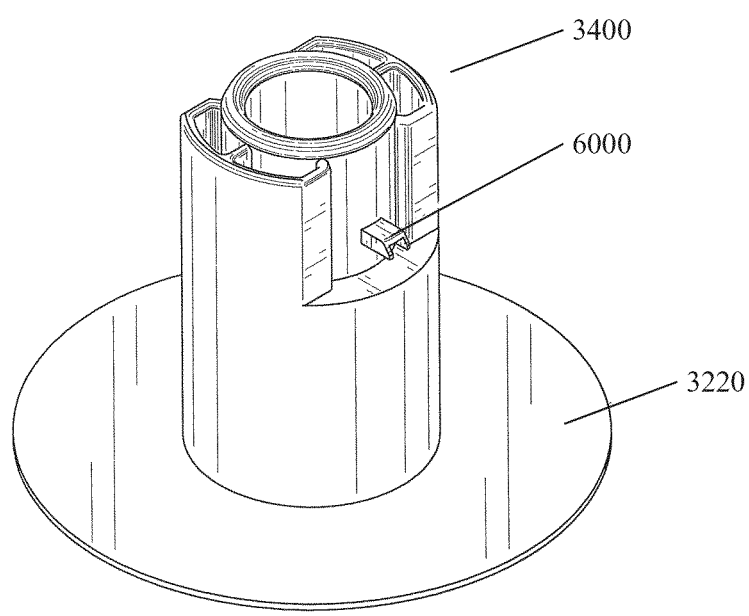
FIG. 16 is a perspective view of the assembled base and locking section.
Figure 17:
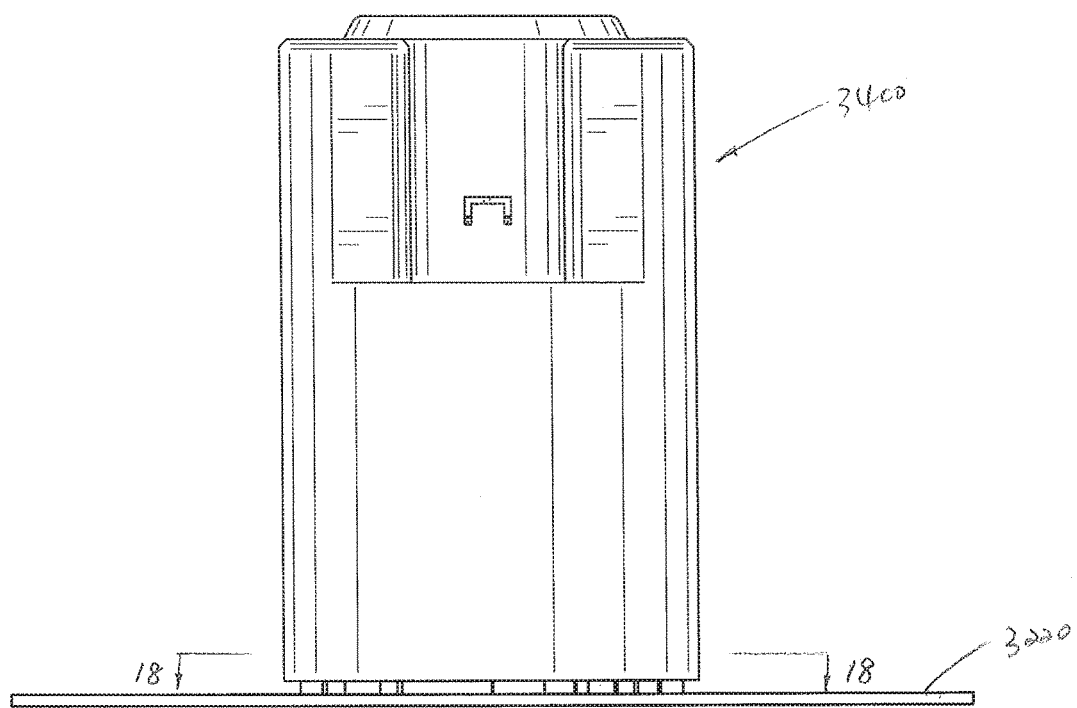
FIG. 17. is a front view of the assembly shown in FIG. 16.
Figure 18:
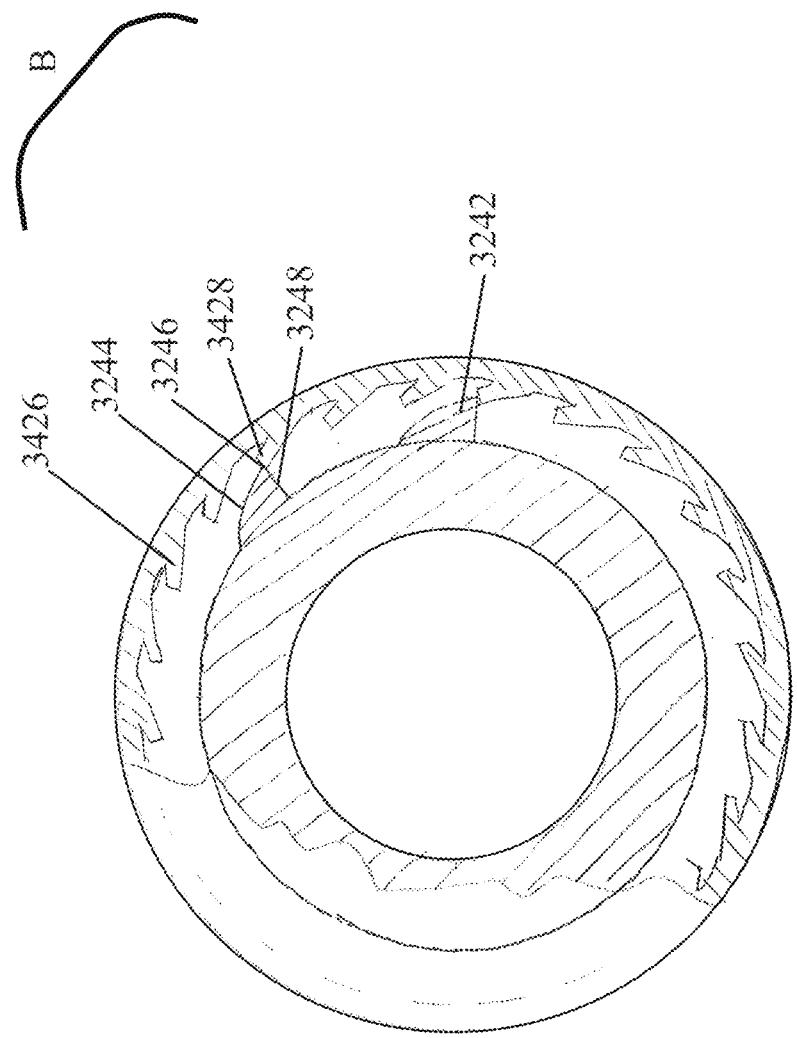
FIG. 18 is a sectional view of the assembly along lines 18-18 of FIG. 17.
Figure 19:
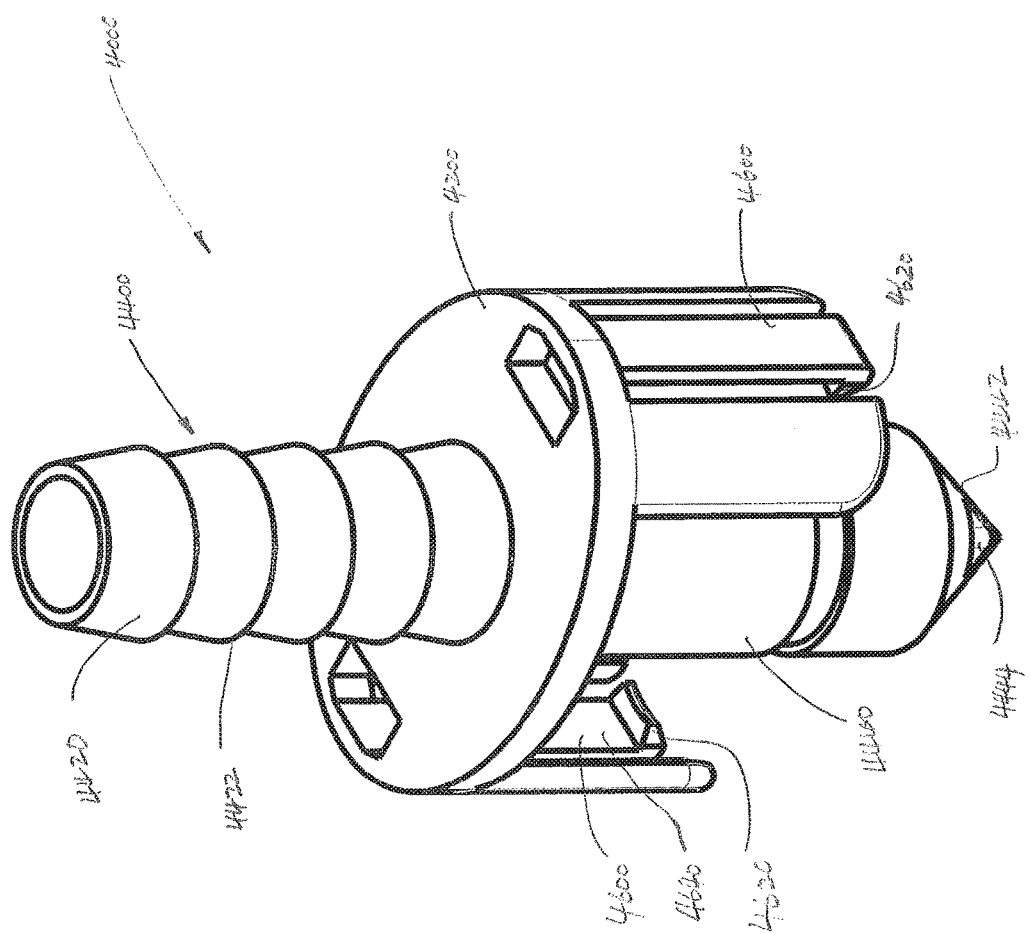
FIG. 19 is a perspective view of the fitting member shown in FIG. 5.
Figure 20:
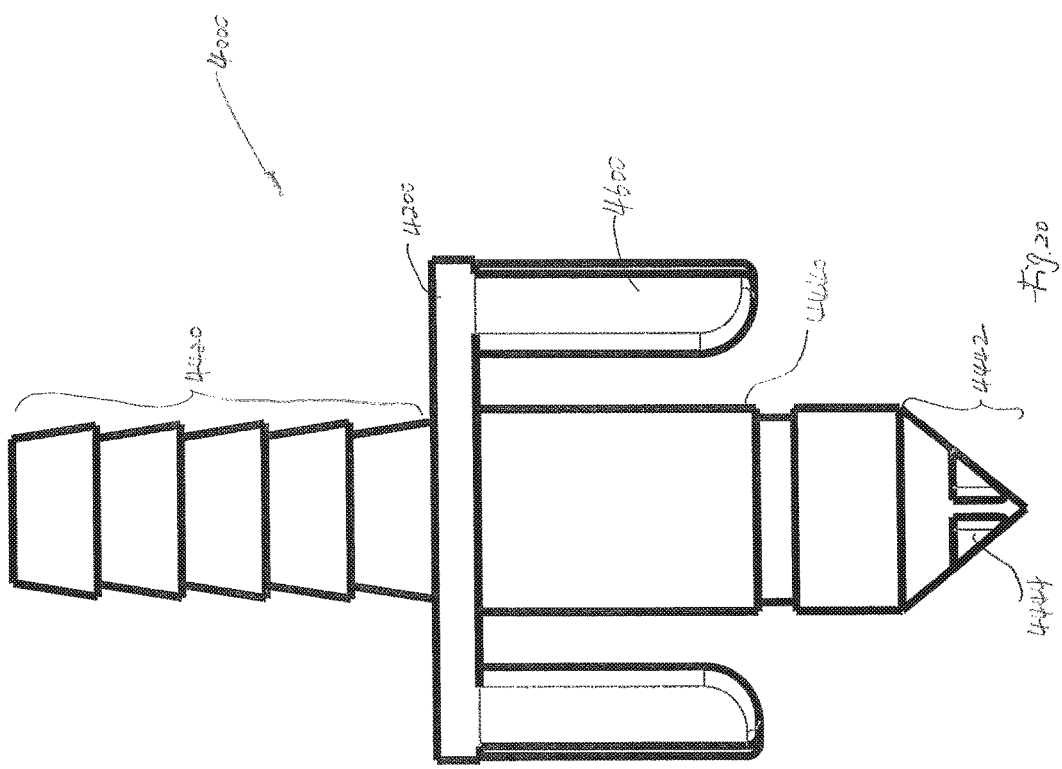
FIG. 20 is a side view of the fitting member shown in FIG. 19.
Figure 21:
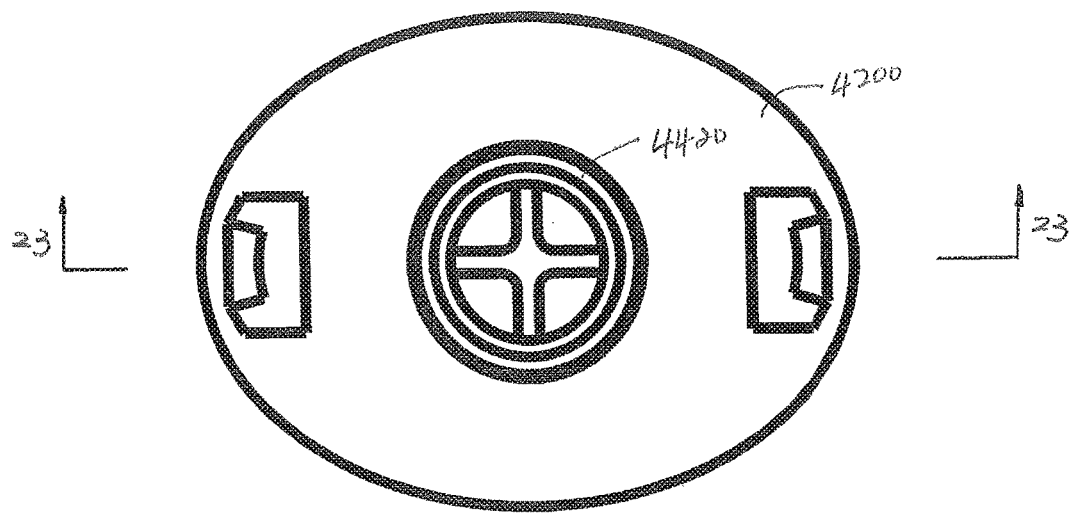
FIG. 21 is a top view of the fitting member shown in FIG. 19.
Figure 22:
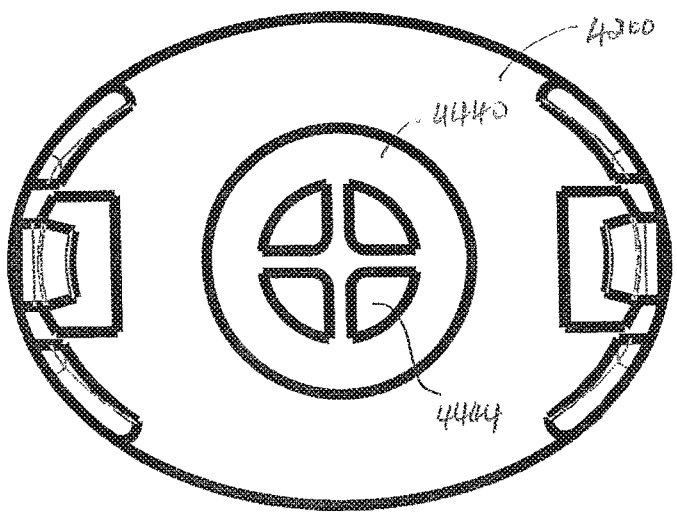
FIG. 22 is a bottom view of the fitting member shown in FIG. 19.

FIG. 16 is a perspective view of the assembly of the base 3200 and the locking section 3400 and FIG. 17 is a front view of the assembly. FIG. 18 is a sectional view of the assembly along lines 18-18 in FIG. 17, which shows the engagement of the tooth 3242 of the base 3200 and the tooth 3426 of the locking section 3400. As the locking section 3400 is threaded to the base 3200 along the direction B, the teeth 3426 start to engage the teeth 3242. As the teeth 3426 engages the teeth 3242, a tip 3428 of the teeth 3426 moves along a first surface 3244 of the teeth 3242. The first surface 3244 can be curved or planar, and is formed to allow the tip 3428 of the teeth 3426 to progressively deform as it moves along the first surface 3244, in view of the material resiliency of the teeth 3426. Consequently, the tip 3428 will pass over the apex 3246 of the teeth 3242 and return to its original position. The teeth 3242 has a second surface 3248, which is adapted to prevent the tip 3428 of the teeth 3426 from moving or rotating reversely and thus, prevent disengagement between the locking section 3400 and the base 3200. After the tip 3428 passes over the apex 3246 and returns to its original position, any attempt to reversely rotate the locking section 3400 with respect to the base 3200 will result in firm abutment of the tip 3428 against the second surface 3248. As shown in FIG. 18, the first surface 3244 presents a gradual slope as opposed to the steep or abrupt slope presented by the second surface 3248.

Referring back to FIGS. 11-14, the upper portion 3440 functions to operatively engage and lock the fitting member 4000. The upper portion 3440 includes a tubular wall 3442 and a pair of supports 3443 disposed radially opposite each other along an external surface 3444 of the tubular wall 3442. For example, the tubular wall 3442 can be a cylindrical wall extending longitudinally along the axis X-X' and the supports 3443 can be disposed radially symmetrically along the external surface 3444 with respect to the axis X-X'. A pair of radially opposite shoulders 3480 are defined between the lower portion 3420 and the upper portion 3440. The upper portion 3440 also has a pair of receiving slots 3445 each for receiving a downwardly extending leg of the fitting member 400. Each receiving slot 3445 is defined by the external surface 3444 of the tubular wall 3442, a corresponding shoulder 3480 and the supports 3443.

The upper portion 3440 further includes a breakable protrusion 6000 provided in each receiving slot 3445. The breakable protrusion 6000 extends radially from the external surface 3444 of the tubular wall 3442 for operatively engaging a locking element of the fitting member 4000, which will be described in connection with the structure of the fitting member 4000. The material and the dimensions of the breakable protrusion 6000 are adapted, such that when the fitting member 4000 is being disconnected from the locking section 3400, the breakable protrusion 6000 will be damaged and break away from the locking section 3400. Thus, a locking reconnection of the connector 3000 to the fitting member 4000 is prevented. As shown in FIG. 4, the fitting member 4000 is positioned in the operation station 1300 below the cartridge 2000 and therefore, without the breakable protrusion 6000, the fitting member 4000 will not stay connected and fall away by force of gravity. The anti-reconnection characteristics of the connector 3000 prevent unauthorized cartridges from being connected to the machine.

The breakable protrusion 6000 includes a first side panel 6200, a second side panel 6400 opposite the first side panel 6200, and a middle panel 6600 connecting the two side panels. Both the first side panel 6200 and the second side panel 6400 are disposed at a same side of the middle panel 6600. In the shown embodiment, both side panels are disposed at the lower side of the middle panel 6600. Both the first side panel 6200 and the second side panel 6400 can be substantially perpendicular to the middle panel 6600. Thus, the side panels and the middle panel collectively define an open space S for receiving the locking element of the fitting member 4000. The first side panel 6200 can include a first sloped surface 6220 and the second side panel 6400 can include a second sloped surface 6420. These sloped surfaces facilitate the engagement between the breakable protrusion 6000 and the locking element of the fitting member 4000, which will be described later in connection with the structural details of the fitting member 4000.

The fitting member 4000 is shown in FIGS. 19-23A. The fitting member 4000 includes a middle plate 4200 and a fluid delivery body 4400 extending through the middle plate 4200. The fluid delivery body 4400 defines within itself a fluid passageway P (shown in FIG. 23), through which lotion can be delivered. The fluid delivery body 4400 is divided by the middle plate 4200 into a first portion 4420 and a second portion 4440.

The first portion 4420 is adapted to engage and mate with the tube 5000, to establish a fluid communication between the fluid passage way P and the tube 5000. In this embodiment, the first portion 4420 includes an uneven, serrated or corrugated external surface 4422, which generates a connective joint between the first portion 4420 and an internal surface of the tube 5000 when the first portion 4420 is inserted into the tube 5000 (see FIG. 4).

The second portion 4440 has a pointed tip 4442 at the terminal end of the second portion extending away from the middle plate 4200. As the fitting member 4000 operatively engages and locks with the locking section 3400 of the connector 3000, the pointed tip 4442 enters the through hole 3460 of the locking section 3400 and pierces through the membrane 3600. One or more openings 4444 are provided to the pointed tip 4442, through which fluid can be transported into the fluid passage way P of the fitting member 4000.

Figure 11:
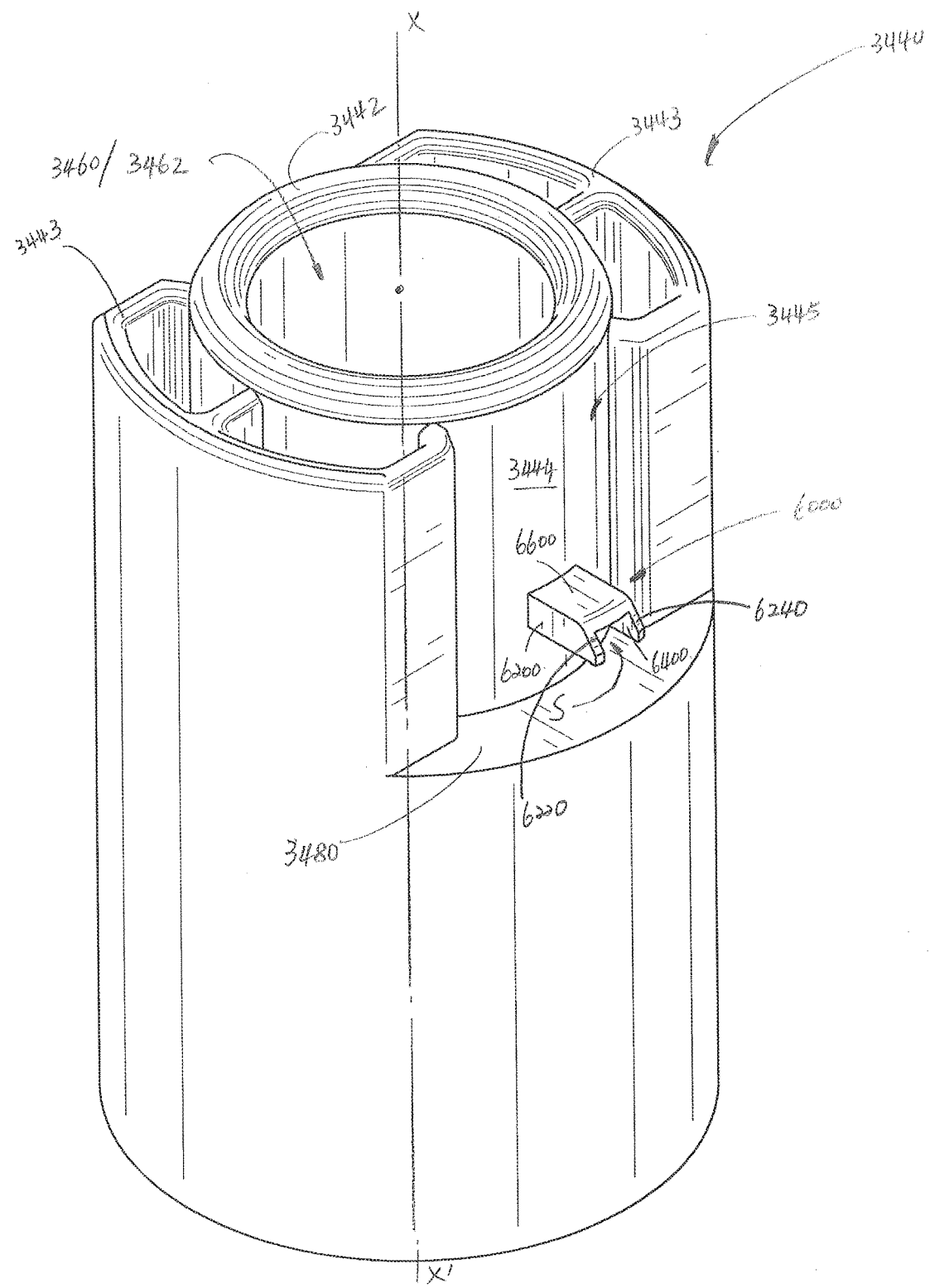
FIG. 11 is a perspective view of a locking section of the connector shown in FIG. 5.
Figure 12:
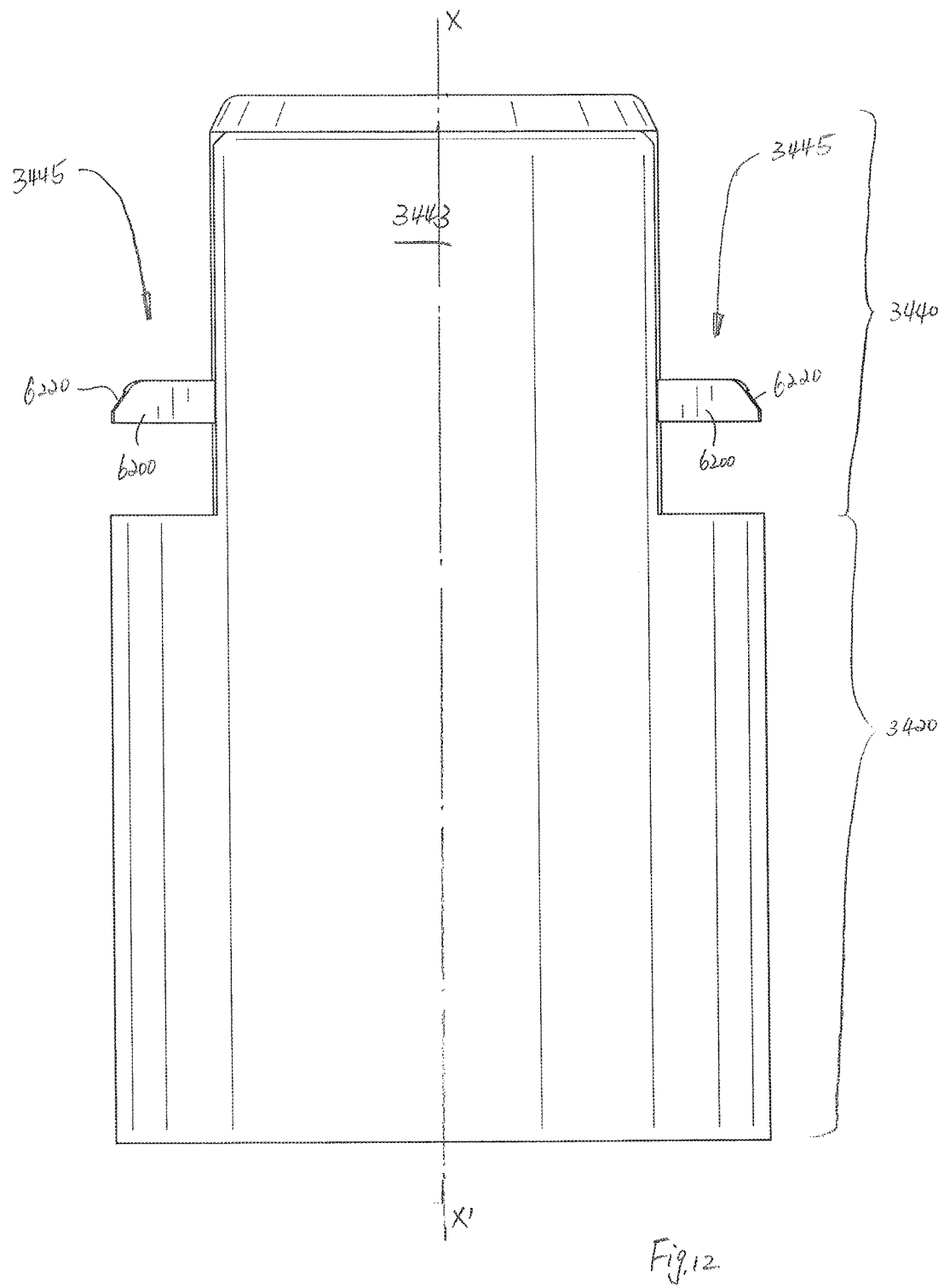
FIG. 12 is a side view of the locking section shown in FIG. 11.
Figure 13:
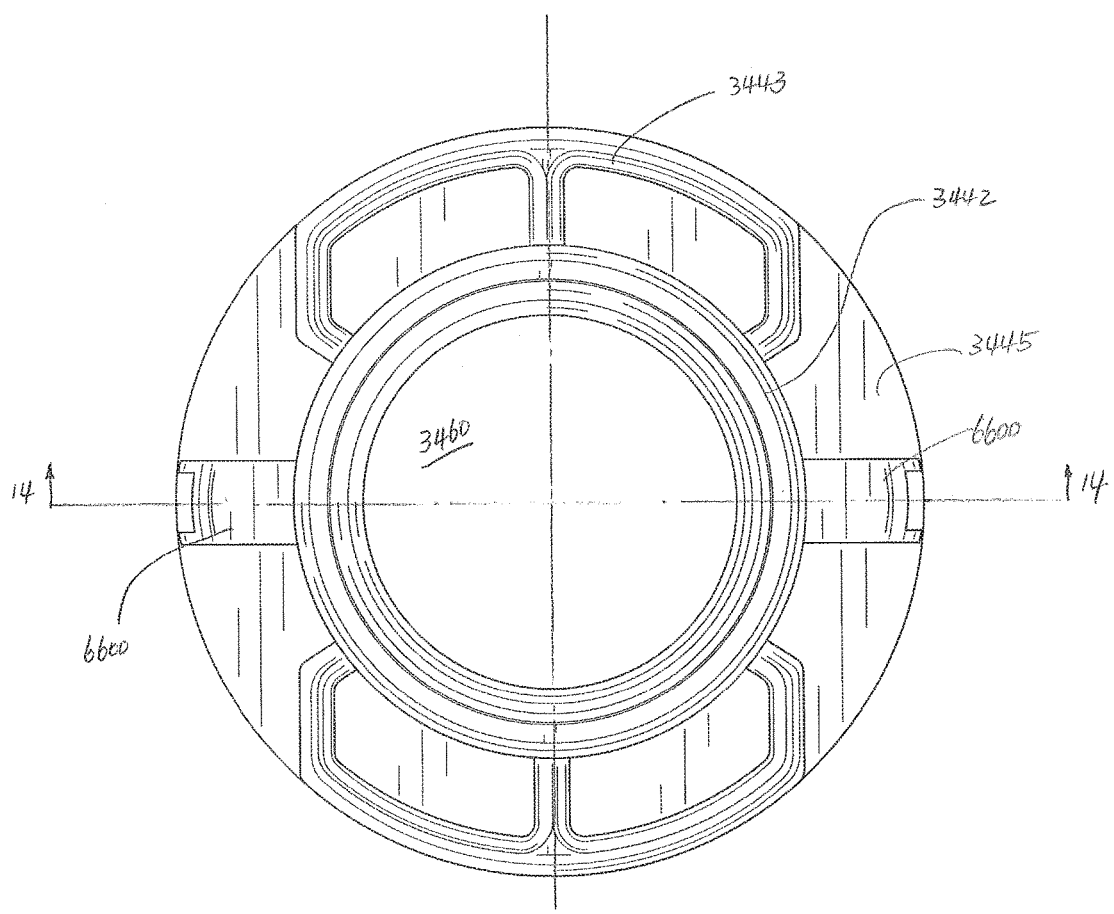
FIG. 13 is a top view of the locking section shown in FIG. 11.

The fitting member 4000 includes at least one locking leg 4600, which extends from the middle plate 4200 and can be inserted into the receiving slot 3445 of the locking section 3400 (see FIG. 11). The locking leg 4600 carries a locking element 4620, which is distanced from the middle plate 4200. The locking element 4620 can be provided on the inner side of the locking leg 4600, the outer side of the locking leg 4600, the distal terminal end of the locking leg 4600, or any other suitable location of the locking leg 4600. In this embodiment, the locking element 4620 is disposed on and extending from an inner surface 4640 of the locking leg 4600.

Figure 24:
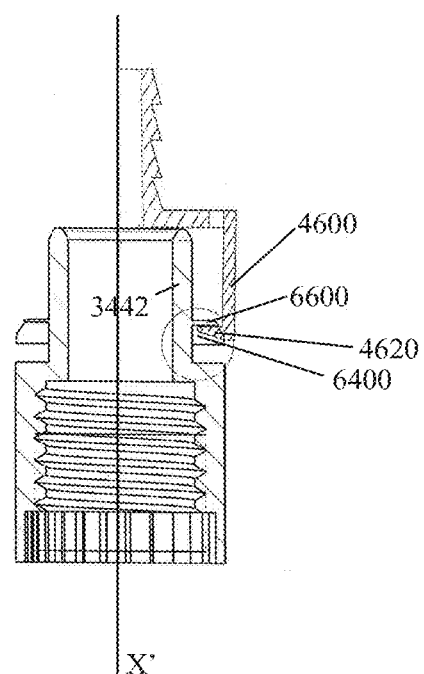
FIG. 24 is a partial sectional view for schematically illustrating a locked configuration of a breakable protrusion of the locking section.
Figure 25:
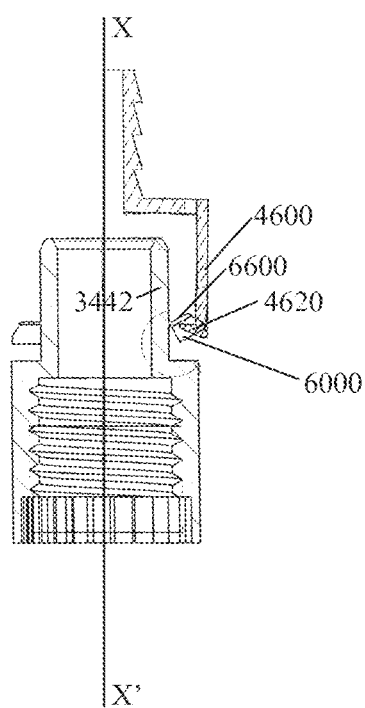
FIG. 25 is a partial sectional view for schematically illustrating a locked configuration of the breakable protrusion.

As the locking leg 4600 is inserted into the receiving slot 3445 to connect the fitting member 4000 to the connector 3000, the locking element 4620 engages the breakable protrusion 6000 to lock the fitting member 4000 with the locking section 3400. In addition, as a predetermined force is applied to disconnect the fitting member 4000 from the locking section 3400 or vice versa, the breakable protrusion 6000 breaks away from the locking section 3400, which prevents reconnection of the same cartridge 2000 to the fitting member 4000. FIG. 24 is a partial sectional view, which schematically illustrates a locked configuration of the breakable protrusion 6000, when the locking element 4620 and the breakable protrusion 6000 engages each other to lock the fitting member 4000 to the connector 3000. FIG. 25 is a partial sectional view, which schematically illustrates a break-away configuration of the breakable protrusion 6000, when the predetermined force is applied to disconnect the fitting member 4000 from the connector 3000. As shown in FIG. 25, in the break-away configuration, the integrity of the breakable protrusion 6000 with the tubular wall 3442 is compromised or damaged. Therefore, the breakable protrusion 6000 no longer has the structural strength and integrity to allow a reconnection and relocking operation of the fitting member 4000 to the connector 3000.

Figure 23A:
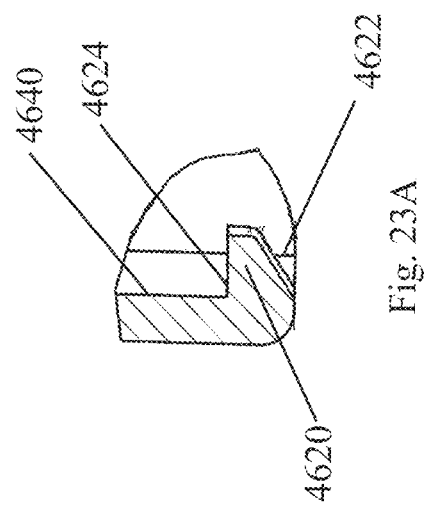
FIG. 23A is a enlarged view of a part A of FIG. 23.
Figure 23:
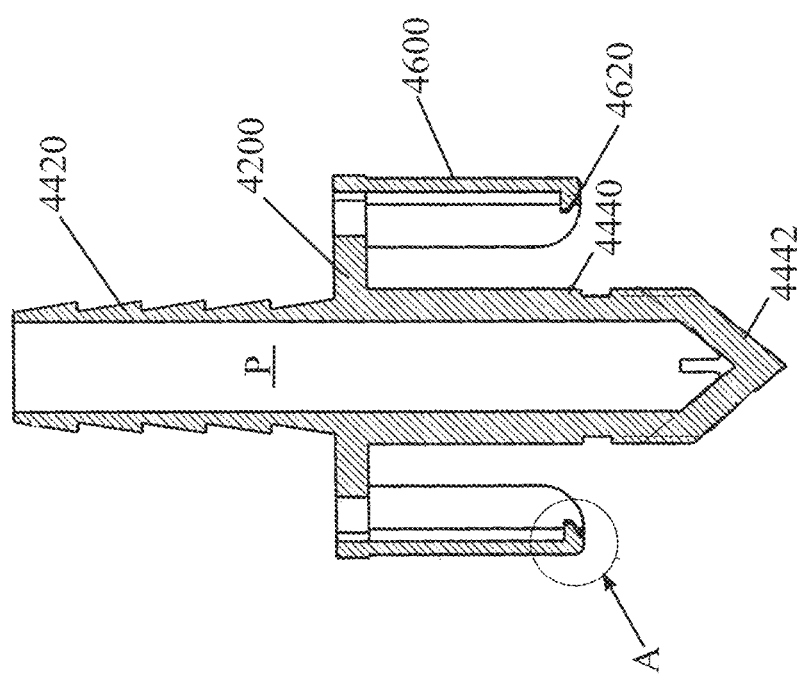
FIG. 23 is a sectional view of the fitting member along lines 23-23 of FIG. 21.

As shown in FIGS. 23 and 23A, the locking element 4620 includes a sloped surface 4622 and a locking surface 4624. The sloped surface 4622 extends angularly with respect to the inner surface 4640. The locking surface 4624 can be substantially perpendicular to the inner surface 4640.

In operation, as the locking leg 4600 advances along the receiving slot 3445 to lock the fitting member 4000 to the locking section 3400, the sloped surface 4622 engages the middle panel 6600 and/or the side panels 6200 and 6400 (particularly, the sloped surfaces 6220 and 6420, see FIG. 11). As the locking leg 4600 is constructed from a material having certain resiliency, this engagement deforms the locking legs 4600 radially outwardly, to allow the locking element 4620 to pass clear of the breakable protrusion 6000. Consequently, as the locking leg 4600 returns to its original position, the locking surface 4624 is placed under the breakable protrusion 6000 to lock the fitting member 4000 to the locking section 3400 of the connector 3000. The locking surface 4624 can engage the undersurfaces of the side panels 6200 and 6400 and/or the undersurface of the middle panel 6600, to temporarily lock the fitting member 4000 to the connector 3000. The locking element 4620 can be adapted to allow the locking element 4620 to be partially or completely received in the space S defined by the middle panel 6600 and the side panels 6200 and 6400.

Since the pointed tip 4442 of the fitting member 4000 penetrates the membrane 3600 simultaneously as the fitting member 4000 locks to the connector 3000, a fluid communication between the cartridge 2000 and the tube 5000 is established, such that the lotion in the container 2200 of the cartridge 2000 can be transported to the tube 5000 and ultimately to the downstream spray nozzles 1294 as controlled by instructions received from the operation station 1300.

When the lotion in the container 2200 is exhausted, the cartridge 2000 can be replaced with a new one. For this purpose, the fitting member 4000 is disconnected from the connector 3000 or vice versa applying a predetermined force to break the locking connection between the locking element 4620 and the breakable protrusion 6000. In this process, the breakable protrusion 6000 is forcefully separated from the locking section 3400. Thus, the fitting member 4000 cannot be re-locked to the connector 3000. Accordingly, reconnection between the fitting member 4000 and the connector 3000 of an exhausted cartridge can be prevented.

Figure 26:
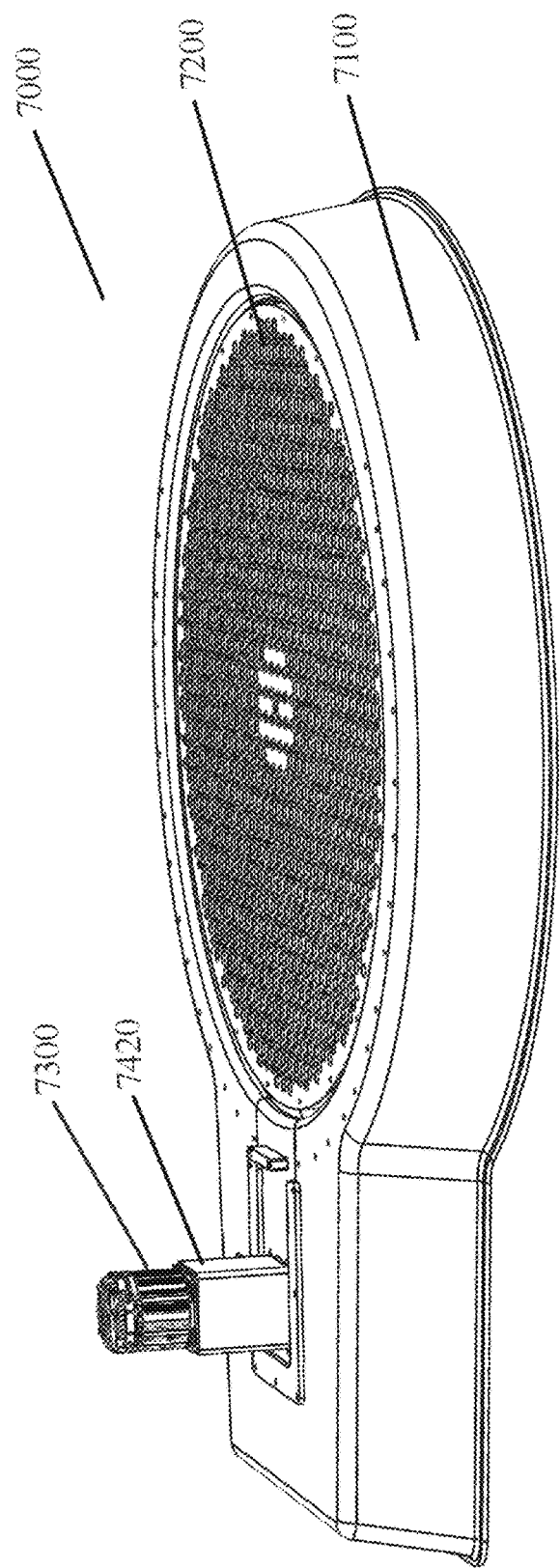
FIG. 26 is a schematic view of a rotatable platform of the lotion application machine according to another aspect of the present application.
Figure 27:
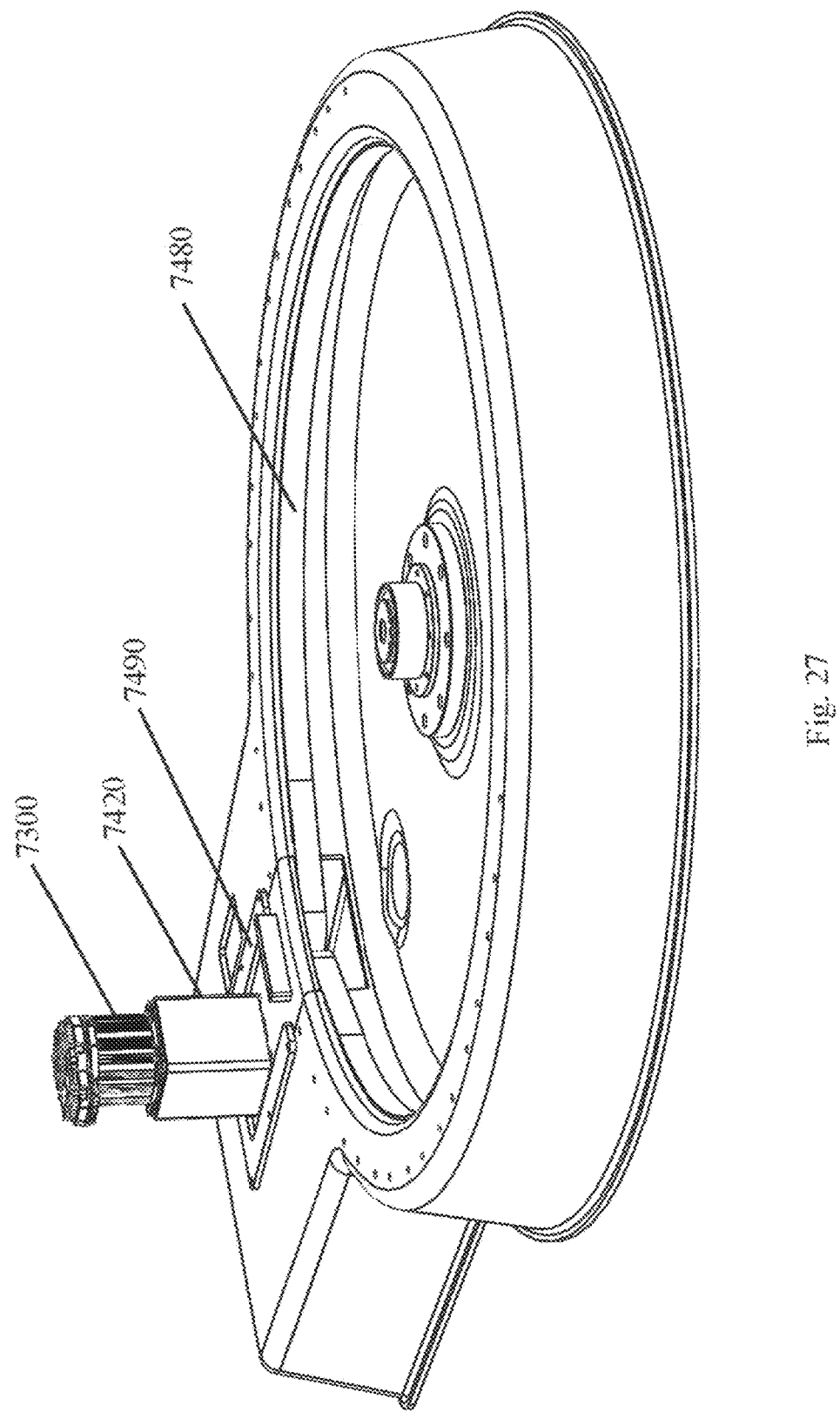
FIG. 27 is another schematic view of the rotatable platform.

According to another aspect of the present disclosure, a lotion application machine having a rotatable platform is provided. FIG. 26 is a schematic view of the rotatable platform 7000, which can be integrated with the lotion application machine 1000 in lieu of the platform 1100. The rotatable platform 7000 allows a user standing on the platform to be rotated in a controlled manner, while lotion is being applied by the lotion applying sections 1290 of the lotion application machine 1000. As a result, the lotion (such as, a sun-screening lotion) can be evenly applied to the entire body of the user.

As shown in FIG. 26, the rotatable platform 7000 includes a fixed portion 7100, which can be fixed to an under-support (such as, the ground or a floor) in a stationary manner. The rotatable platform 7000 further includes a rotatable portion 7200, which is rotatable with respect to the fixed portion 7100. The rotatable portion 7200 can be substantially circular. The fixed portion 7100 provides structural support for the wall 1200 and the control station 1300.

The rotation of the rotatable portion 7200 with respect to the fixed portion 7100 is implemented by a power supply and transmission system, which includes a power supplier 7300 and a power transmission 7400. As shown in FIG. 26, the power supplier 7300 can be, for example, a servo motor. The servo motor is constructed and/or programmed to receive a control signal (which can be inputted by the user through the interface 1332 of the control station 1320) and after being energized by electrical power, to rotate an output shaft at a predetermined RPM (revolution per minute) based on the received control signal.

Figure 28:
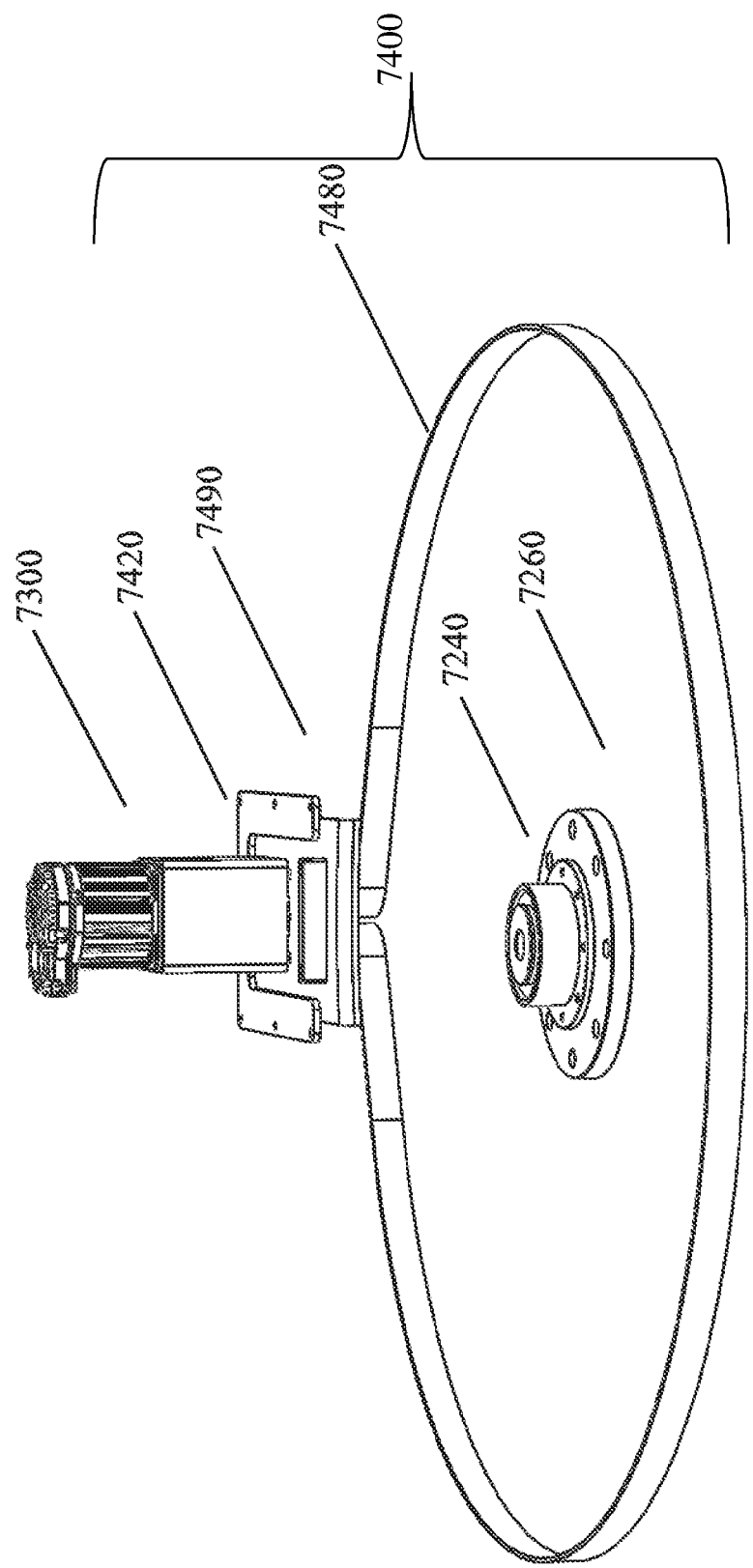
FIG. 28 is still another schematic view of the rotatable platform.
Figure 29:
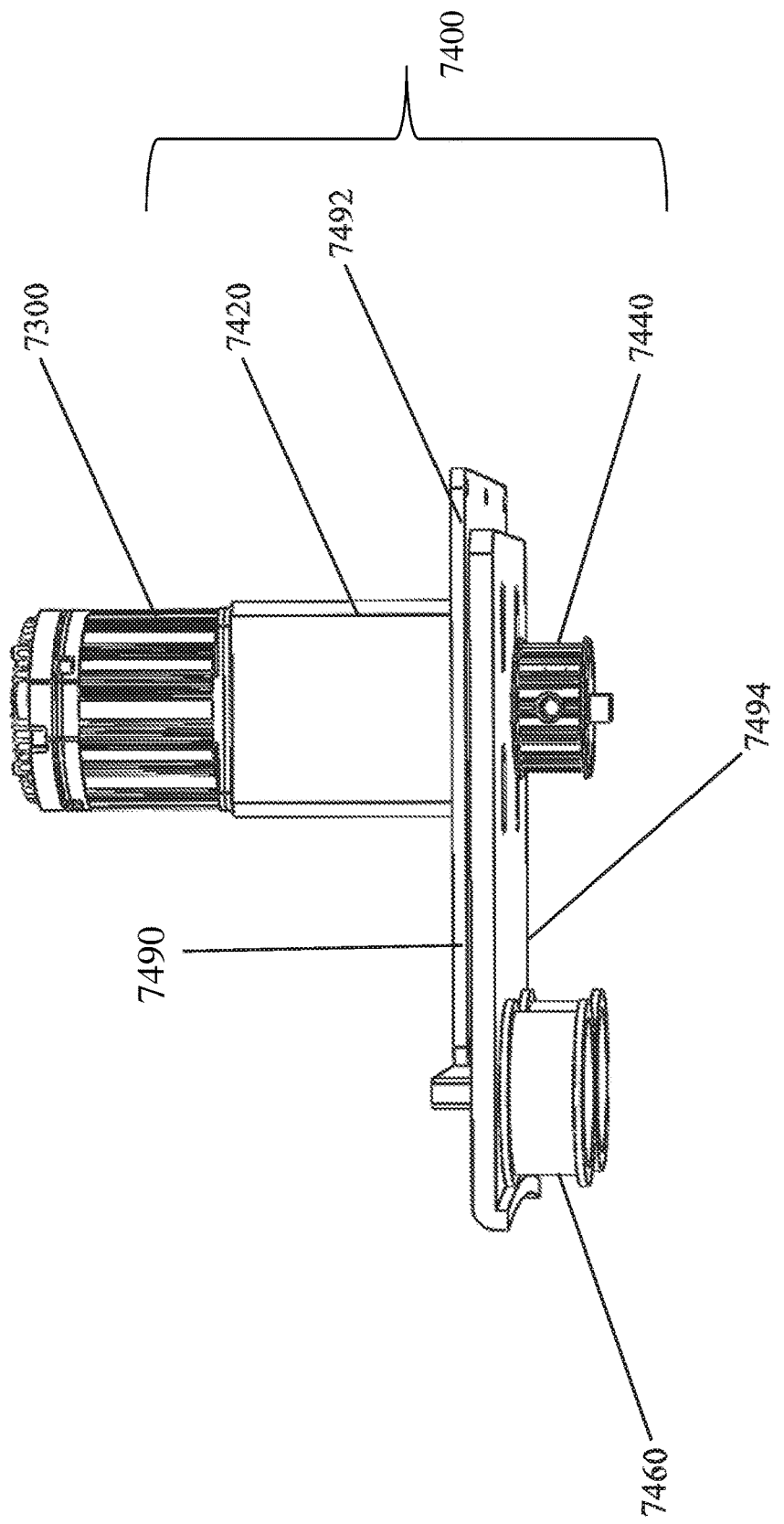
FIG. 29 is a schematic view of a power supply and transmission system of the rotatable platform.

As shown in FIGS. 27-32, the power transmission 7400 includes a gearbox 7420, a timing pulley 7440, a pair of idler pulleys 7460 and an endless belt 7480. The gearbox 7420 can be integrally formed with the servo motor 7300. As shown in FIG. 29, the servo motor 7300, the gearbox 7420, the timing pulley 7440 and the idler pulleys 7460 can be mounted to a mount plate 7490 to improve the integrity of the power supplying and transmission system of the rotatable platform 7000. In the shown embodiment, the gearbox 7420 is mounted to a top surface 7492 of the mount plate 7490; the timing pulley 7440 and the idler pulleys 7460 are mounted to a bottom surface 7494 of the mount plate 7490. An input shaft of the gearbox 7420 is connected to and driven by the output shaft of the servo motor 7300, such that the rotation of the output shaft of the servo motor 7300 can be transmitted to the input shaft of the gearbox 7420. The gearbox can include various combinations of gears of different parameters to control the rotation speed and the torque of an output shaft of the gearbox 7420.

Figure 30:
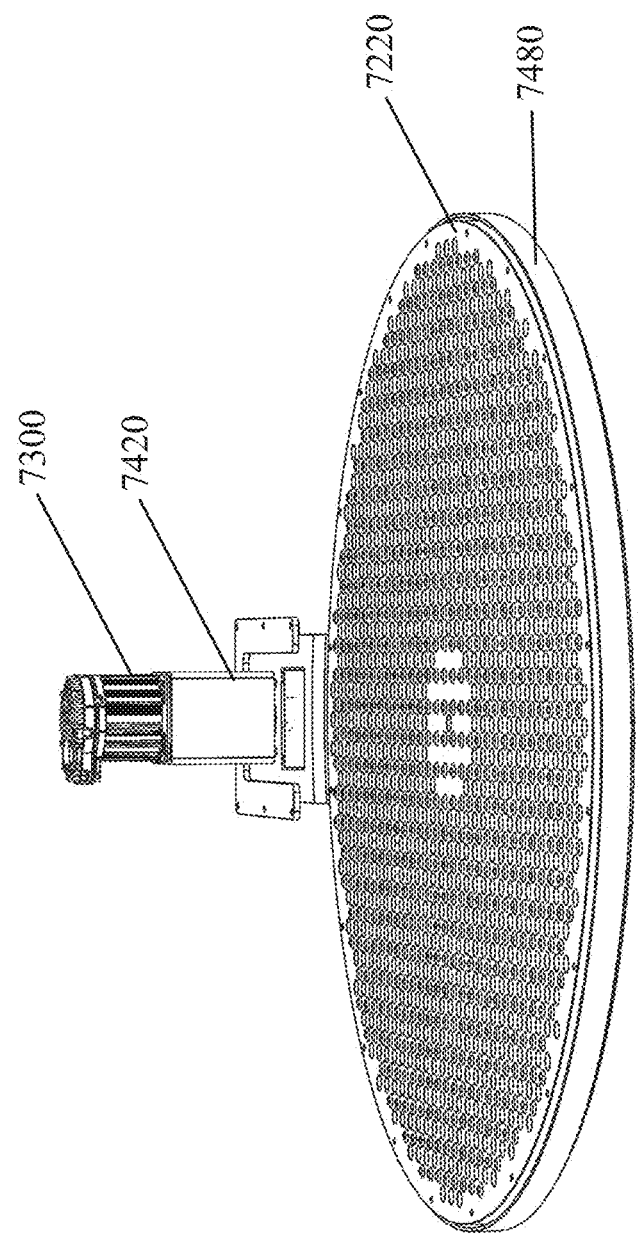
FIG. 30 is another schematic view of the power supply and transmission system of the rotatable platform.

As shown in FIG. 30, the endless belt 7480 is wrapped around an outer circumference 7220 of the rotatable portion 7200 (or alternatively, placed in a groove formed around the outer circumference 7220), such that the endless belt 7480 can be tensioned to rotate the rotatable portion 7200 through frictional engagement between the endless belt 7480 and the outer circumference 7220. As shown in FIG. 28, the rotatable portion 7200 can have a center bearing 7240 and a bearing spindle 7260, such that the rotatable portion 7200 is rotatable about an axis of the center bearing 7240.

Figure 31:
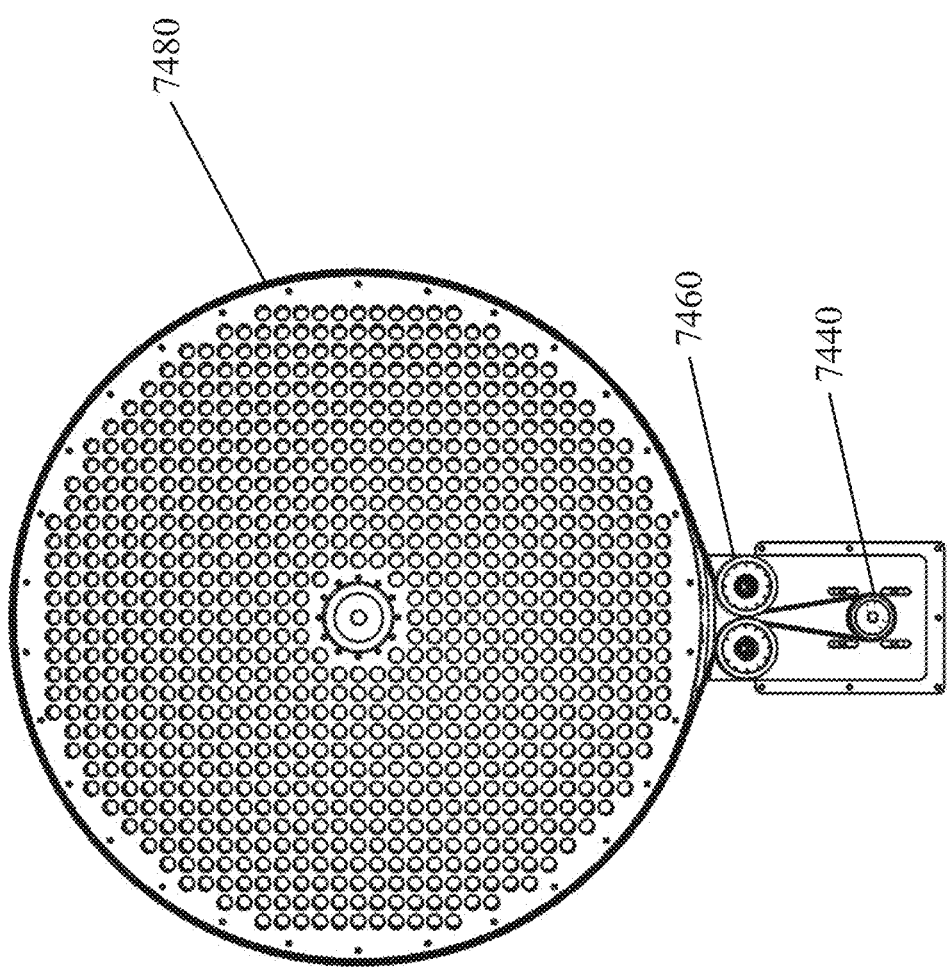
FIG. 31 is a bottom schematic view of the rotatable platform.
Figure 32:
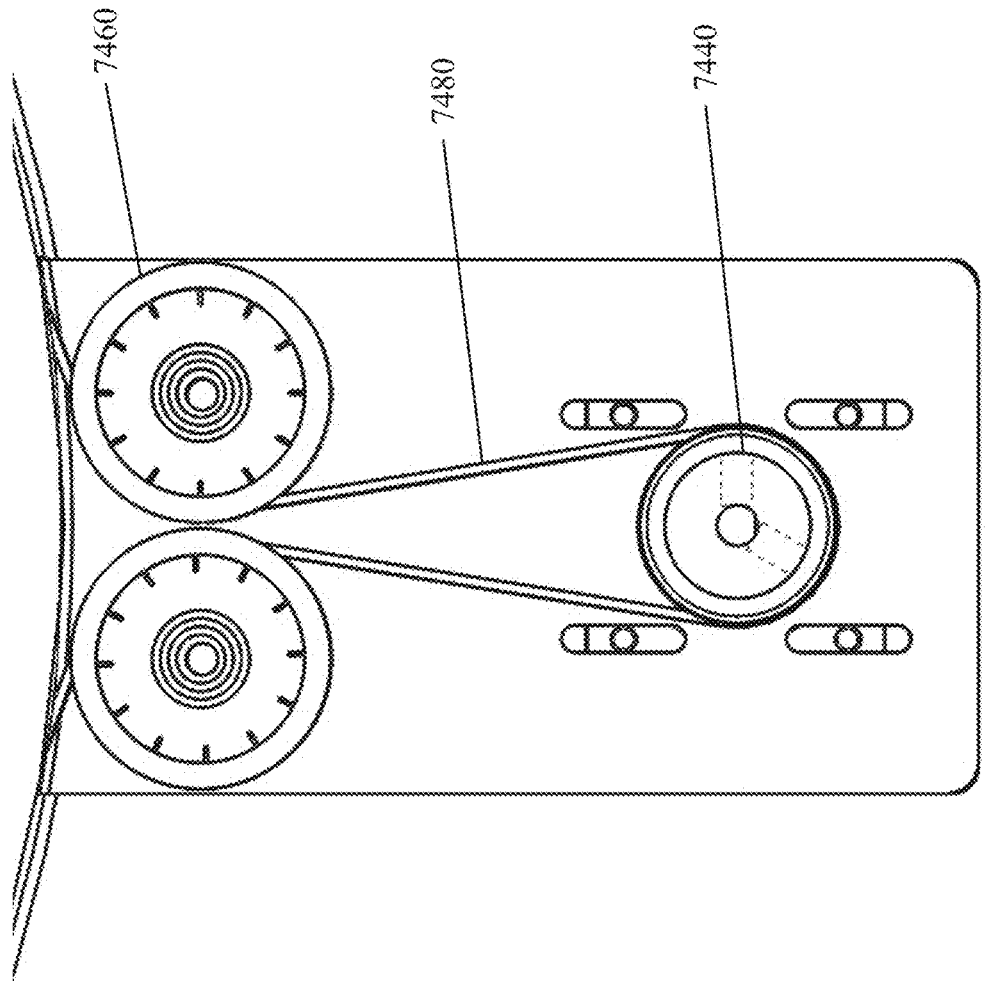
FIG. 32 is an enlarged schematic view of the rotatable platform.

As shown in FIGS. 31 and 32, the endless belt 7480 is also wrapped around the timing pulley 7440. In addition, the endless belt 7480 passes through the idler pulleys 7460 to engage the idler pulleys 7460. The timing pulley 7440 is connected to the output shaft of the gearbox 7420 and functions to drive the movement of the endless belt 7480 by engaging and tensioning the endless belt 7480, which in turn drives the rotation of the rotatable portion 7200 of the rotatable platform 7000. The idler pulleys 7460 serve to guide the movement of the endless belt 7480 and selectively assist in tensioning the endless belt 7480, by engaging the endless belt 7480.

The power supply and transmission system of the rotatable platform 7000 (which includes the servo motor 7300, the gearbox 7420, the timing pulley 7440 and the idler pulleys 7460) can be constructed to be movable to adjust its space from the rotatable portion 7200 of the rotatable platform 7000. As a result, the tension of the endless belt 7480 can be adjusted to allow the endless belt 7480 to be securely wrapped around the outer circumference 7220 of the rotatable portion 7200.

Although the lotion application machine, the cartridge and the rotatable platform have been described with respect to applying lotion, especially sunscreen, a person of ordinary skill in the art understands that they can be used to transport and apply any suitable fluid.

The features of the present invention as applied to various specific embodiments thereof have been shown and described. It will also be understood that various omissions, substitutions and changes in the form and details of the devices illustrated and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A lotion application system comprising:
a lotion application machine; and
a platform for receiving the lotion application machine, wherein the platform has a top surface for supporting a user of the lotion application machine;
wherein the lotion application machine comprises:
a continuous circumference provided on the platform for defining a lotion application space;

at least one lotion applicator provided on the continuous circumference and comprising at least one spray nozzle for spraying a lotion into the lotion application space;

a cartridge for storing the lotion;

a tubing for delivering the lotion from the cartridge to the at least one lotion applicator, wherein the tubing comprising a fitting for detachably connecting the cartridge to the tubing; and an operation station comprising a user interface for allowing the user to activate the at least one lotion applicator to spray the lotion into the lotion application space, wherein the platform comprises:

a fixed portion secured to an under-support, wherein the continuous circumference is provided on the fixed portion;

a rotatable portion rotatable with respect to the fixed portion, wherein the rotatable portion has the top surface for supporting the user; and a power supply and transmission system for rotating the rotatable portion with respect to the fixed portion, wherein the power supply and transmission system comprises a power supply and a power transmission for transmitting the power generated by the power supply to the rotatable portion for rotating the rotatable portion, wherein the power transmission comprises:

a timing pulley configured to receive the power generated by the power supply and rotate upon receiving the power generated by the power supply;

an endless belt wrapped around the timing pulley to be moved by the rotation of the timing pulley, wherein the endless belt is wrapped around an outer circumference of the rotatable portion to rotate the rotatable portion through engagement with the outer circumference of the rotatable portion; and a pair of idler pulleys, wherein the pair of idler pulleys are configured to engage the endless belt to guide the movement of the endless belt and selectively tension the endless belt;

wherein the power supply comprises:

a servo motor having an output shaft, wherein the servo motor is configured to receive a control signal and generate predetermined rotation of the output shaft based on the control signal;

wherein the power transmission further comprises:

a gearbox comprising a plurality of gears and an output shaft, wherein the gearbox is configured to receive the predetermined rotation of the output shaft of the servo motor and generate a predetermined rotation of the output shaft of the gearbox, wherein the timing pulley is attached to the output shaft of the gearbox to rotate the timing pulley.

2. The lotion application system according to claim 1, further comprising an anti-slip layer on the top surface of the platform.

3. The lotion application system according to claim 1, wherein the continuous circumference is defined by a wall upstanding from the platform and the at least one lotion applicator is mounted on the wall.

4. The lotion application system according to claim 3,
wherein the wall comprises a first lateral end and an opposite second lateral end; and
wherein the second lateral end is attached to the operation station.

5. The lotion application system according to claim 3,
wherein the at least one lotion applicator comprises a plurality of columns circumferentially distributed along an inner side of the wall; and
wherein the at least one spray nozzle comprises a plurality of spray nozzles mounted on the plurality of columns, respectively.

6. The lotion application system according to claim 1,
wherein the power supply and transmission system further comprises a mount plate; and
wherein the servo motor and the gearbox are mounted to a top surface of the mount plate and the timing pulley and the idler pulleys are mounted to a bottom surface of the mount plate.

7. The lotion application system according to claim 1, wherein the power supply and transmission system are configured to be movable with respect to the rotatable portion for adjusting the tension applied to the endless belt.

* * * * *